(12) United States Patent
Basson et al.

(10) Patent No.: US 12,048,703 B2
(45) Date of Patent: Jul. 30, 2024

(54) USE OF SMALL MOLECULE FAK ACTIVATORS TO PROMOTE MUCOSAL HEALING

(71) Applicants: Regents of the University of Minnesota, Minneapolis, MN (US); University of North Dakota, Grand Forks, ND (US)

(72) Inventors: Marc D. Basson, Grand Forks, ND (US); Vadim J. Gurvich, Apple Valley, MN (US)

(73) Assignee: University of North Dakota, Grand Forks, ND (US)

( * ) Notice: Subject to any disclaimer, the term of this patent is extended or adjusted under 35 U.S.C. 154(b) by 25 days.

(21) Appl. No.: 17/047,237

(22) PCT Filed: Nov. 13, 2018

(86) PCT No.: PCT/US2018/060765
§ 371 (c)(1),
(2) Date: Oct. 13, 2020

(87) PCT Pub. No.: WO2019/199353
PCT Pub. Date: Oct. 17, 2019

(65) Prior Publication Data
US 2021/0161907 A1 Jun. 3, 2021

Related U.S. Application Data

(60) Provisional application No. 62/657,215, filed on Apr. 13, 2018.

(51) Int. Cl.
*A61K 31/5377* (2006.01)
*A61K 31/40* (2006.01)
*A61P 1/04* (2006.01)
*A61P 17/02* (2006.01)

(52) U.S. Cl.
CPC .......... *A61K 31/5377* (2013.01); *A61K 31/40* (2013.01); *A61P 1/04* (2018.01); *A61P 17/02* (2018.01)

(58) Field of Classification Search
CPC .................. A61K 31/40; A61P 1/04
See application file for complete search history.

(56) References Cited

U.S. PATENT DOCUMENTS

2017/0304237 A1* 10/2017 Zhang .................. C07D 207/27

FOREIGN PATENT DOCUMENTS

WO WO-2019199353 A1 10/2019

OTHER PUBLICATIONS

"Database Registry [Online]", Chemical Abstracts Service, Columbus, Ohio, US; XP002788347 Database accession No. 1301763-47-2, (May 27, 2011).
"Database Registry [Online]", Chemical Abstracts Service, Columbus, Ohio, US; XP002788348 Database accession No. 1371916-00-5, (May 1, 2012).
"Database Registry [Online]", Chemical Abstracts Service, Columbus, Ohio, US; XP002788349 Database accession No. 1388549-34-5, (Aug. 9, 2012).
"International Application Serial No. PCT/US2018/060765, International Search Report mailed Feb. 20, 2019", 4 pgs.
"International Application Serial No. PCT/US2018/060765, Written Opinion mailed Feb. 20, 2019", 6 pgs.
Khan, MD Rafiqul Islam, et al., "Activation of focal adhesion kinase via M1 muscarinic acetylcholine receptor is required in restitution of intestinal barrier function after epithelial injury", Biochimica Et Biophysica Acta. Molecular Basis of Disease, vol. 1842, No. 4, (Dec. 21, 2013), 635-645.
Raschka, S, et al., "Introduction", Journal of Physiology and Pharmacology : An Official Journal of the Polish Physiological Society, vol. 69, No. 2, (Apr. 1, 2018), 1-9.
Yanju, MA, et al., "Focal adhesion kinase regulates intestinal epithelial barrier function via redistribution of tight junction", Biochimica Et Biophysica Acta Jan. 2013, vol. 1832, No. 1, (Oct. 12, 2012), 151-159.
"International Application Serial No. PCT/US2018/060765, International Preliminary Report on Patentability mailed Oct. 22, 2020", 8 pgs.

\* cited by examiner

*Primary Examiner* — Theodore R. Howell
(74) *Attorney, Agent, or Firm* — Schwegman Lundberg & Woessner, P.A.

(57) ABSTRACT

Methods to activate or enhance phosphorylation of focal adhesion kinase (FAK) are provided herein. Methods to treat epithelial disorders in mammals, namely diseases of the gut, comprising the administration of one or more small molecules having FAK activation properties are also provided.

6 Claims, 8 Drawing Sheets

Fig. 1C: D3 (10 nM) accelerates circular wound closure in Caco-2 monolayers on collagen I *when proliferation is blocked by 4mM OH-urea*. (*p<0.05, n=24 pooled from 3 separate studies)

Fig. 1D: D3 does not stimulate Caco-2 proliferation at 48 hours (and in fact tends to decrease it). (n=24 pooled from 3 separate studies)

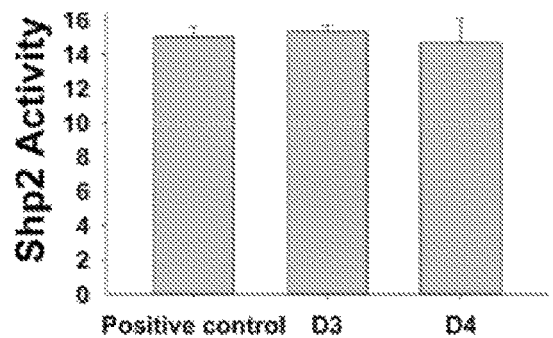
Fig 1G: Neither D3 nor D4 (100 nM) blocks SHP2 dephosphorylation of a synthetic substrate vs. positive control reaction without D3 or D4.
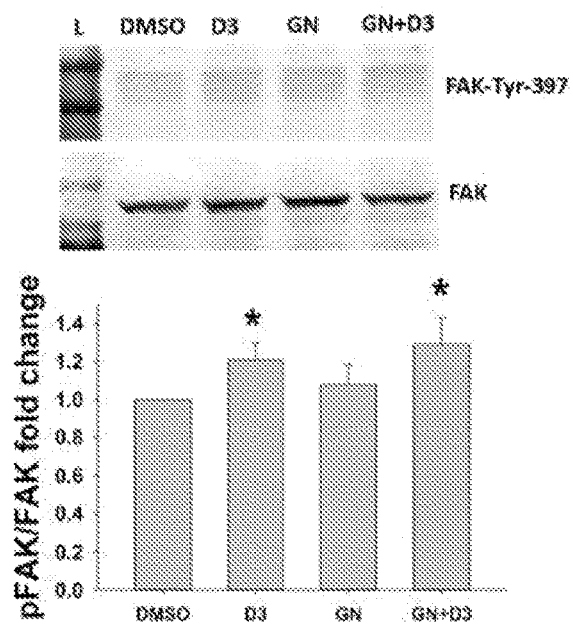
Fig 1F: 100ug/ml genistein does not block D3 activation of FAK in human Caco-2 intestinal epithelial cells (n-6, *p<0.05).

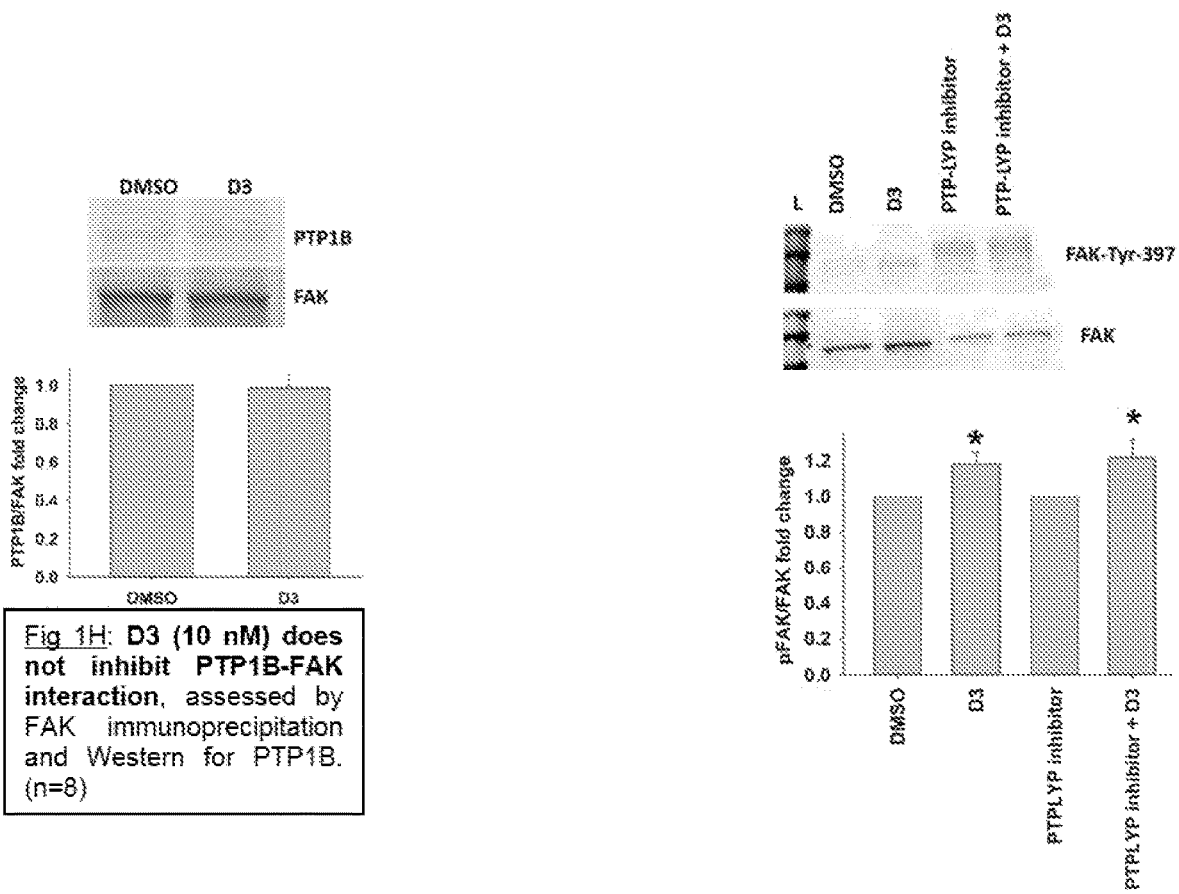
FIG. 1I
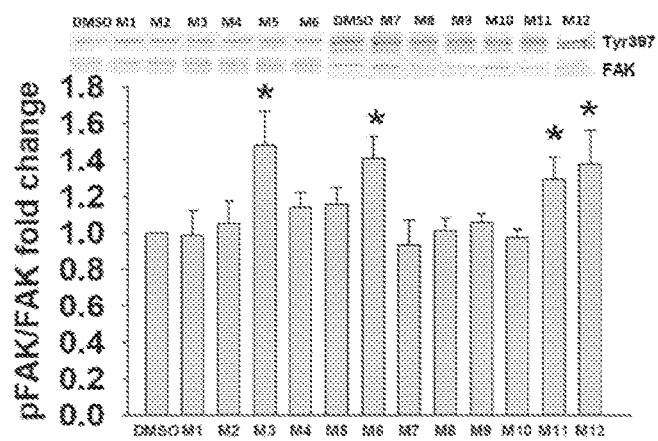

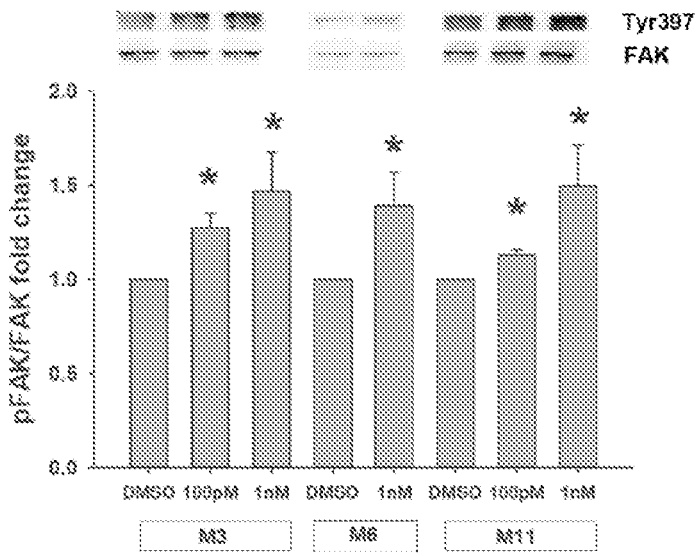
Fig 1K: M3, M6, M11 activate FAK phosphorylation even at 100 pm-1nM. (n>5,*p<0.05; lower doses & M12 untested)
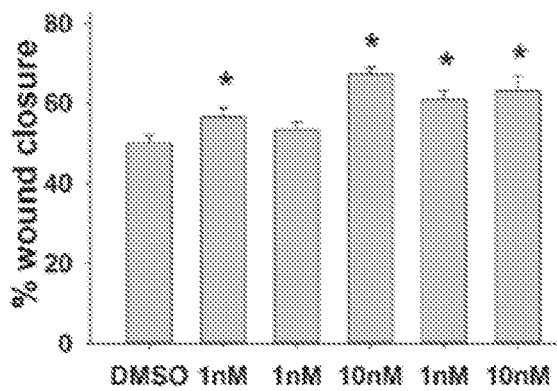
Fig 1L: M3, M6, and M11 promote Caco-2 monolayer wound closure. (n>5,*p<0.05; lower doses & M12 untested)

Day 4 DMSO    Day 4 D3

DMSO (day 4)    D3 (day 4)

USE OF SMALL MOLECULE FAK ACTIVATORS TO PROMOTE MUCOSAL HEALING

CROSS-REFERENCE TO RELATED APPLICATIONS

This application is a U.S. National Stage Filing under 35 U.S.C. 371 from International Application No. PCT/US2018/060765, filed on Nov. 13, 2018, and published as WO 2019/199353 on Oct. 17, 2019, which application claims the benefit of priority to U.S. Provisional Appl. Ser. No. 62/657,215, filed Apr. 13, 2018, which are incorporated by reference as if fully set forth herein.

BACKGROUND

Inadequate intestinal mucosal healing contributes to diverse and common disease states, including peptic ulcer, Crohn's disease, ulcerative colitis, celiac disease, necrotizing enterocolitis, and the loss of the mucosal barrier in critical illness that contributes to bacterial translocation and septic states. The failure to heal a mucosal injury can result in loss of bowel or even life. One example would be the patient hospitalized with an acute flare of Crohn's disease, who is managed medically for a few days with even more aggressive immunosuppression and then taken to surgery if that fails. This not only subjects the patient to a surgical procedure with attendant pain and morbidity, but irretrievably reduces the amount of small intestine available for nutrient absorption. This may ultimately lead to short gut syndrome if subsequent disease flares require repeated resections.

Healing represents an equilibrium between the processes that injure the bowel mucosa (inflammation, ischemia, and luminal agents) and the epithelial sheet migration and proliferation for resurfacing injured gut. However, virtually all current approaches to managing mucosal injury focus on reducing injury (e.g. immunosuppressives, anti-acid agents).

SUMMARY

The present invention is directed to pharmacological activation of focal adhesion kinase (FAK) using small molecules and the promotion of mucosal healing via the regulation of FAK. For example, provided herein is pharmacological intervention to activate or enhance the phosphorylation of FAK, thereby accelerating mucosal healing. Treatment of epithelial disorders, namely gastrointestinal conditions affecting mucosal surfaces such as Crohn's disease, ulcerative colitis, and peptic ulcer disorder in mammals, is also contemplated herein.

One embodiment provides methods for treating epithelial disorders in a subject in need thereof, namely gut disorders, via the administration of small molecule compounds that promote mucosal healing through the regulation (e.g., positive) of focal adhesion kinase (FAK). Such administration may be accomplished in any number of ways, including without limitation intraperitoneal, intravenous, oral, rectal, or by way of nasogastric or enteric tubes.

Some embodiments provide a method to treat an epithelial disease or a method to activate focal adhesion kinase phosphorylation in eukaryotic cells comprising contacting cells or administering to a subject in need thereof an effective amount of a compound of Formula I:

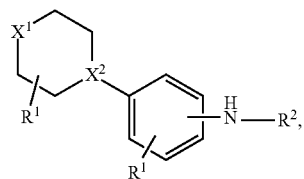

wherein
$X^1$ and $X^2$ are independently —C— or —N—; and
$R^1$ and $R^2$ are independently chosen from —H, —OH, and substituted or unsubstituted ($C_1$-$C_{20}$) hydrocarbyl.

In some embodiments, the ($C_1$-$C_{20}$)hydrocarbyl is chosen from ($C_1$-$C_{20}$)alkyl, ($C_1$-$C_{20}$)alkenyl, ($C_1$-$C_{20}$)alkynyl, ($C_1$-$C_{20}$)acyl, ($C_1$-$C_{20}$)cycloalkyl, ($C_1$-$C_{20}$)aryl, ($C_1$-$C_{20}$)alkoxy, ($C_1$-$C_{20}$)haloalkyl, and combinations thereof.

In some embodiments, the compound is represented by Formula II:

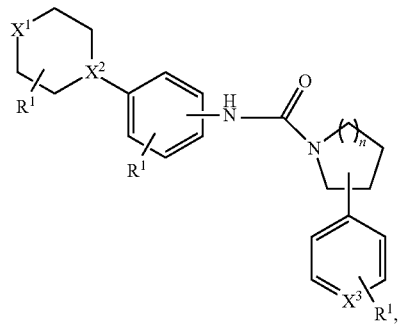

wherein
$X^3$ is —C— or —N—; and
n is 1 or 2.

In some embodiments, the compound is represented by a compound of Formula IX:

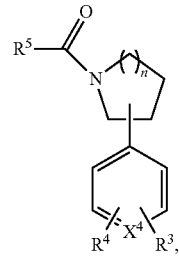

wherein
$X^4$ is —C— or —N—; and
$R^3$, $R^4$, $R^5$ are independently chosen from —H, —OH, and substituted or unsubstituted ($C_1$-$C_{20}$) hydrocarbyl; and
n is 1 or 2.

In some embodiment, the ($C_1$-$C_{20}$)hydrocarbyl is chosen from ($C_1$-$C_{20}$)alkyl, ($C_1$-$C_{20}$)alkenyl, ($C_1$-$C_{20}$)alkynyl, ($C_1$-$C_{20}$)acyl, ($C_1$-$C_{20}$)cycloalkyl, ($C_1$-$C_{20}$)aryl, ($C_1$-$C_{20}$)alkoxy, ($C_1$-$C_{20}$)haloalkyl, and combinations thereof.

BRIEF DESCRIPTION OF THE DRAWINGS

FIG. 1C depicts D3 at 10 nM accelerates closure of circular wounds in Caco-2 monolayers on collagen I when proliferation is blocked by 4 mM OH-urea (*$p<0.05$, $n=24$ pooled from 3 separate studies).

FIG. 1D depicts treatment with D3 does not stimulate Caco-2 proliferation at 48 hours (and tends to decrease it) ($n=24$ pooled from 3 separate studies).

FIG. 1F depicts that 100 ug/ml genistein does not block D3 activation of FAK in human Caco-2 intestinal epithelial cells ($n=6$, *$p<0.05$).

FIG. 1G demonstrates that neither D3 nor D4 (100 nM) blocks SHP2 dephosphorylation of a synthetic substrate vs. positive control reaction without D3 or D4.

FIG. 1H demonstrates that D3 (10 nM) does not inhibit PTP1B-FAK interaction, assessed by FAK immunoprecipitation and Western for PTP1B ($n=8$).

FIG. 1I shows that 10 nM D3 stimulates Caco-2 FAK-Y-397 phosphorylation independently of PTP PEST inhibition by PTP LYP inhibitor 540217 (50 uM) ($n=6$, *$p<0.05$).

FIG. 1J demonstrates that 10 nM M3, M6, M11, M12 activate FAK Y-397 phosphorylation ($n=6$; *$p<0.05$).

FIG. 1K is a bar graph showing that M3, M6, M11 activate FAK phosphorylation even at 100 pm-1 nM ($n=5$, *$p<0.05$; lower doses and M12 were untested).

FIG. 1L provides a bar graph depicting data that M3, M6 and M11 promote Caco-2 monolayer wound closure ($n=5$, *$p<0.05$; lower doses and M12 were untested).

DESCRIPTION

Figure 1A:
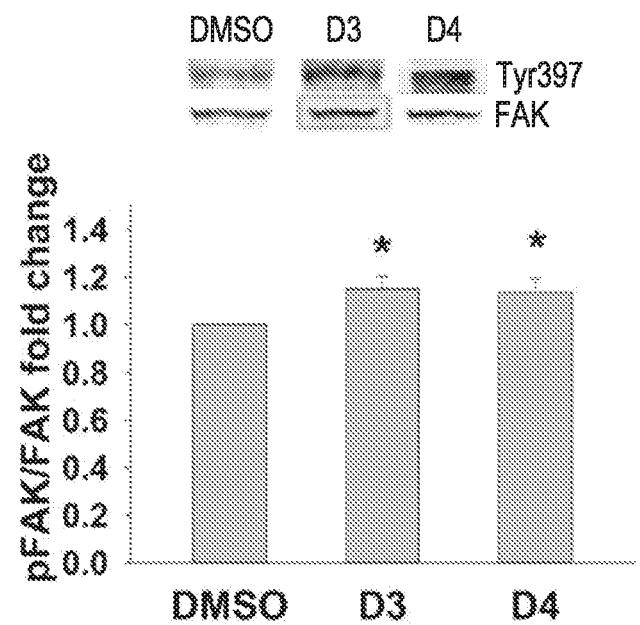
FIG. 1A depicts that D3 and D4 at 10 nM activate FAK (assessed as FAK-Tyr-397 phosphorylation) in Caco-2 intestinal epithelial cells in suspension (*$p<0.05$, $n=8$). D1 and D2 also activated FAK.

Failure of mucosal healing is central to diseases as diverse as inflammatory bowel disease (IBD), peptic ulcer, and necrotizing enterocolitis (NEC). Failure to heal substantially impairs quality of life in patients with these diseases, may require risky surgery, and even kills patients. Approximately 1 million people in the US are afflicted with IBD (1), and 51,200 died of IBD in the US alone in 2013 (2). Healing of GI mucosal injury represents an equilibrium between injurious agents and the migration and proliferation of epithelial cells at the wound edge. Most treatments, such as antacids or antisecretory drugs for ulcers, anti-inflammatory agents for IBD, attempt to minimize further injury. However, intact mucosa resists noxious stimuli more effectively than mucosa in which the mucosal barrier has been breached. Therefore, promoting mucosal healing by epithelial sheet migration is a potentially synergistic target. Surprisingly, despite significant research carried out in the area of factors and cytokines, there are no therapeutic agents promoting mucosal healing directly in treating IBD, peptic ulcer, NEC, or other gut mucosal lesions. Therefore, developing a new therapy to promote mucosal healing is an important unmet medical need affecting a substantial number of patients both nationally and worldwide.

Healing of GI mucosal injury represents an equilibrium between injurious agents and the migration and proliferation of epithelial cells at the wound edge. Most treatment attempts to minimize further injury (e.g. antacids or anti-secretory drugs for ulcers, anti-inflammatory agents for IBD). However, intact mucosa resists noxious stimuli more effectively than mucosa in which the mucosal barrier has been breached, so promoting mucosal healing by epithelial sheet migration is a potentially synergistic target. Surprisingly, despite all of the scientific work that has been done with growth factors and cytokines, no currently available therapeutic agents promote mucosal healing directly in treating IBD, peptic ulcer, NEC, or other gut mucosal lesions.

Focal adhesion kinase (FAK), a nonreceptor protein tyrosine kinase, is expressed in most tissues and cell types and is highly conserved across mammalian and other eukaryotic species (Schaller M D (2010) J Cell Sci 123:1007-1013). The phosphorylation of FAK's tyrosine and serine residues in response to integrin engagement, mitogenic neuropeptides, lysophosphatidic acid, platelet-derived growth factor, activated Rho, and selected oncogenes leads to the formation of docking sites for a variety of signaling molecules that may regulate cell morphology, locomotion, proliferation, differentiation, and apoptosis (Schaller M D; Parsons J T (2003) J Cell Sci 116:1409-1416; Hanks S K, Polte T R (1997) Bioessays 19:137-145).

Focal adhesion kinase (FAK) is a regulator of epithelial sheet migration. FAK activation is a convergent target for many growth factors (3) and inhibiting (4) or reducing (5) FAK inhibits migration. However, activated FAK is decreased in migrating intestinal epithelial cells in vitro (4) and at the edge of human mucosal ulcers (6), making FAK an attractive target to promote mucosal healing. While searching for small molecules that would mimic a subdomain of the N-terminal FERM domain of FAK and therefore competitively inhibit FAK-AKT binding (7), two small molecules were identified that actually activate FAK at concentrations as low as 10 nM. Follow-up structure-activity relationship study using commercially available analogs (SAR by commerce) identified additional compounds that similarly activate FAK at nanomolar to picomolar levels, as well as a structural framework for compounds with such activity. The compounds investigated for further testing promoted epithelial sheet migration in vitro. In vivo testing was also carried out. The compounds markedly accelerated mucosal ulcer healing in two mouse models without obvious toxicity. It is believed that these compounds mimic part of the FERM domain and act by interfering with the FAK FERM domain inhibition of the FAK kinase domain. These compounds provide for a novel treatment to promote mucosal healing in diseases such as IBD, peptic ulcer, ischemic colitis, and NEC.

Mucosal healing involves epithelial motility, proliferation, and differentiation. Focal adhesion kinase (FAK) influences all three. FAK is an autophosphorylating tyrosine kinase that mediates downstream signals by receptors for matrix proteins and many growth factors and can promote epithelial cell motility, a first step in mucosal healing. Many studies have focused on FAK activation within minutes after ligand binding to FAK-associated membrane receptors. Studies have suggested that FAK may be regulated at the protein level as well as in its phosphorylation during gut epithelial cell motility in vitro and during mucosal healing in vivo. Little has heretofore been known about the regulation of FAK protein levels. It has been hypothesized that integrin- and FAK-related signal events regulate FAK protein pools at the mRNA level, by modulating FAK gene transcription or FAK mRNA degradation, and that TGFβ stimulates FAK by acting on this pathway. A control point for regulation of intracellular FAK protein and mRNA pools during intestinal epithelial motility has been characterized, and the role of protein levels of this molecule in gut epithelial wound healing has been demonstrated. A previously unknown pathway by which intestinal epithelial cell motility is regulated and its specific modulation by TGFβ has also been characterized.

Provided herein are FAK-activating agents/compounds that can specifically promote epithelial restitution and mucosal healing, thereby treating/healing mucosal injury either without or in synergistic combination with immunosuppressives.

Compounds

Provided herein is the further development of the observation that certain small molecules/compounds that mimic the tertiary structure of one subdomain of FAK result in its increased activation (5). No currently available therapeutic specifically activates FAK, although numerous growth factors and cytokines are noted to activate FAK along with many other signals within the cell. No currently available agent directly and specifically promotes intestinal epithelial sheet migration and mucosal healing. While tyrosine phosphatase inhibitors are known, and indeed Novartis has a SHP-2 inhibitor in clinical trials for cancer (8), the molecules/compounds provided herein do not appear to exert their actions by inhibiting tyrosine phosphatases (low levels of inhibition may occur) which would be expected to result in the activation of multiple kinases other than FAK but appear to promote the activation of FAK itself. (Indeed, preliminary data shows SHP-2 is not inhibited and a PTP-PEST inhibitor does not block the effect.) This selectivity permits substantially higher doses with less toxicity.

An in-silico screen of the ZINC12 database (Irwin, Sterling, Mysinger, Bolstad and Coleman, J. Chem. Inf. Model. 2012 DOI: 10.1021/ci3001277) of available small molecules/compounds was conducted, seeking molecules with some structural homology to either of a 33-amino acid subdomain or a 7-amino acid peptide of FAK previously characterized as being of interest as potential FAK inhibitors in a study of an unrelated pathway. A number of candidate molecules were observed to have activated basal FAK.

Four such representative molecules are provided in the table below:

| Compound | ZINC ID | IUPAC Name | Structure |
| --- | --- | --- | --- |
| 1 | ZINC31501681 | N-[(1S)-3-oxo-1-phenyl-3-[(2S)-2-([1,2,4]triazolo[4,3-a]pyridin-3-yl)pyrrolidin-1-yl]propyl]benzamide | 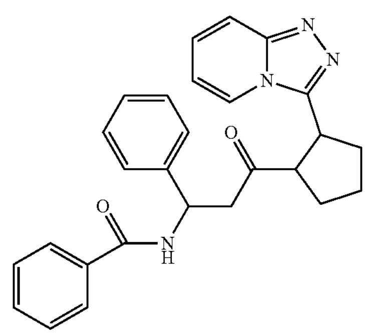 [SMILES: O=C(NC(CC(=O)C1CCCC1c1nnc2ccccn12)c1ccccc1)c1ccccc1] |
| 2 | ZINC58264388 | [(1S)-3-[(2S)-2-(2-methylphenyl)pyrrolidin-1-yl]-3-oxo-1-thiophen-2-ylpropyl]urea | 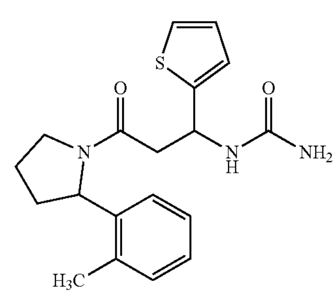 [SMILES: Cc1ccccc1C1CCCN1C(=O)CC(NC(N)=O)c1cccs1] |

| Compound | ZINC ID | IUPAC Name | Structure |
|---|---|---|---|
| 3 | ZINC40099027 | 2-(4-methoxyphenyl)-N-[2-(morpholin-4-yl)-5-(trifluoromethyl)phenyl]pyrrolidine-1-carboxamide | 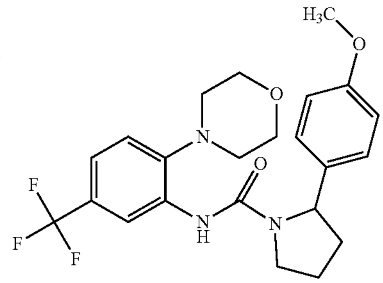 [SMILES: COc1ccc(C2CCCN2C(=O)Nc2cc(C(F)(F)F)ccc2N2CCOCC2)cc1] |
| 4 | ZINC25613745 | 1-(2-chlorophenyl)-3-[2-(3,4-dimethoxyphenyl)pyrrolidin-1-yl]-3-oxopropylurea | 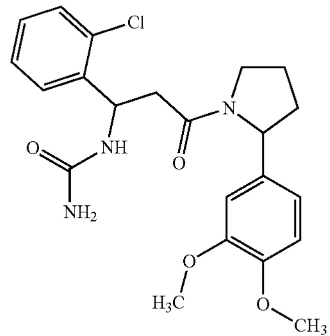 [SMILES: COc1ccc(C2CCCN2C(=O)CC(NC(N)=O)c2ccccc2Cl)cc1OC] |

D3 and D4 were found to be especially potent: D3: ZINC40099027 (2-(4-methoxyphenyl)-N-[2-(morpholin-4-yl)-5-(trifluoromethyl)phenyl]pyrrolidine-1-carboxamide); D4: ZINC25613745 (1-(2-chlorophenyl)-3-[2-(3,4-dimethoxyphenyl)pyrrolidin-1-yl]-3-oxopropylurea).

Additional examples of compounds of the invention include:

M3  CAS 1301763-47-2
    CID 53536016
    MW 420.436

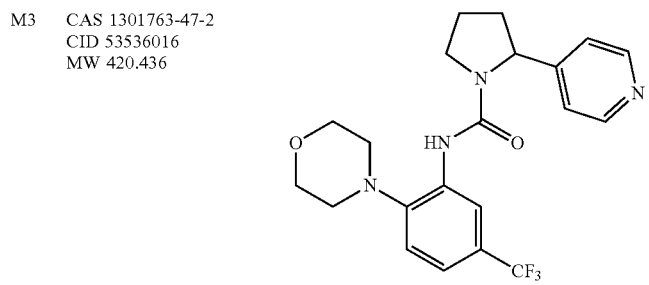

M6  CAS 1371916-00-5
    CID: 60446729
    MW 466.505

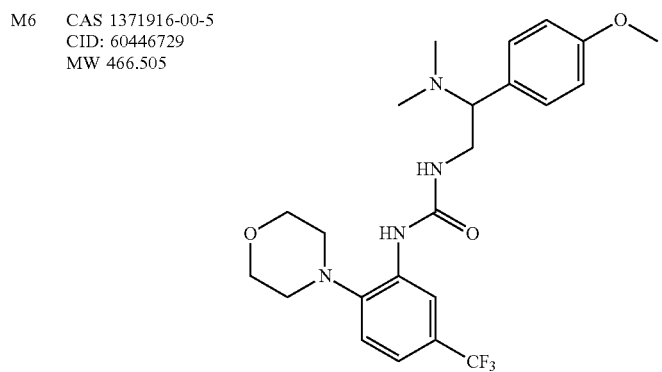

M11 CAS 1388549-34-5
CID 60486055
MW 425.496

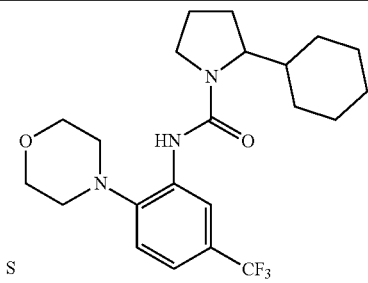

M12 No CAS CID
MW 419.4457

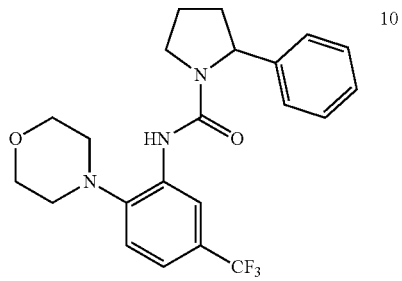 [SMILES: O=C(Nc1cc(C(F)(F)F)ccc1N1CCOCC1)N1CCCC1c1ccccc1]

Also provided herein are compounds of the following formula(s):

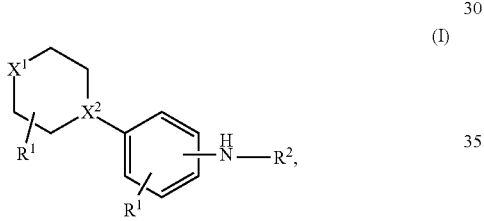
(I)

wherein
X$^1$ and X$^2$ are independently —C— or —N—; and
R$^1$ and R$^2$ are independently chosen from —H, —OH, and substituted or unsubstituted (C$_1$-C$_{20}$) hydrocarbyl.

In some embodiments, the (C$_1$-C$_{20}$)hydrocarbyl is chosen from (C$_1$-C$_{20}$)alkyl, (C$_1$-C$_{20}$)alkenyl, (C$_1$-C$_{20}$)alkynyl, (C$_1$-C$_{20}$)acyl, (C$_1$-C$_{20}$)cycloalkyl, (C$_1$-C$_{20}$)aryl, (C$_1$-C$_{20}$)alkoxy, (C$_1$-C$_{20}$)haloalkyl, and combinations thereof.

In other embodiments, the compound is represented by Formula II:

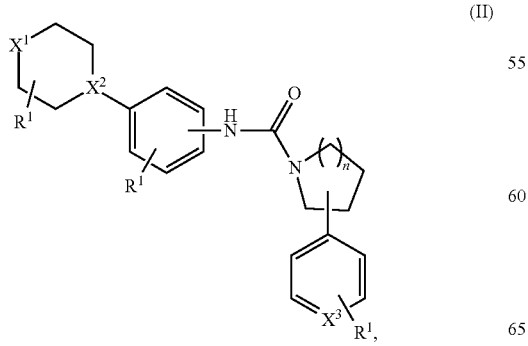
(II)

wherein
X$^3$ is —C— or —N—; and
n is 1 or 2.

In some embodiments, the compound is represented by Formula III:

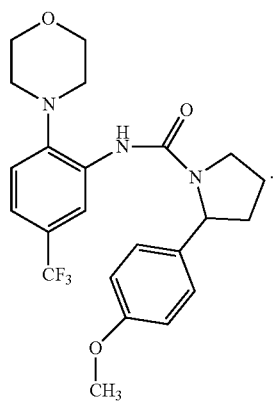
(III)

In other embodiments, the compound is represented by Formula IV:

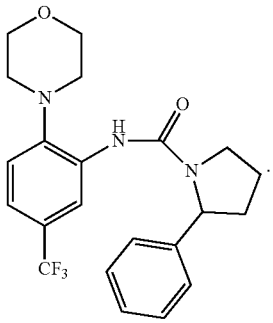

(IV)

In some embodiments, the compound is represented by Formula V:

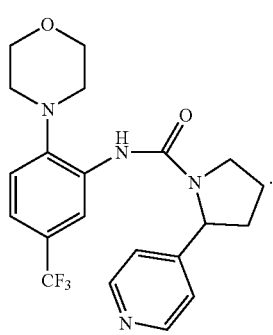

(V)

In some embodiments, the compound is represented by Formula VI:

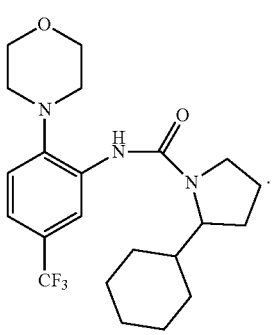

(VI)

In some embodiments, the compound is represented by Formula VII:

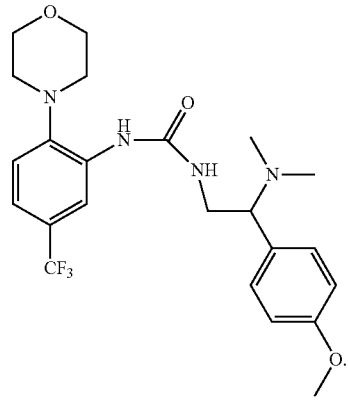

(VII)

In some embodiments, the compounds are represented by Formula IX:

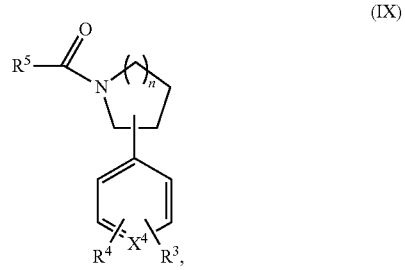

(IX)

wherein
X$^4$ is —C— or —N—; and
R$^3$, R$^4$, R$^5$ are independently chosen from —H, —OH, and substituted or unsubstituted (C$_1$-C$_{20}$) hydrocarbyl; and
n is 1 or 2.

In some embodiments, the (C$_1$-C$_{20}$)hydrocarbyl is chosen from (C$_1$-C$_{20}$)alkyl, (C$_1$-C$_{20}$)alkenyl, (C$_1$-C$_{20}$)alkynyl, (C$_1$-C$_{20}$)acyl, (C$_1$-C$_{20}$)cycloalkyl, (C$_1$-C$_{20}$)aryl, (C$_1$-C$_{20}$)alkoxy, (C$_1$-C$_{20}$)haloalkyl, and combinations thereof.

In some embodiments, the compound is represented by Formula X:

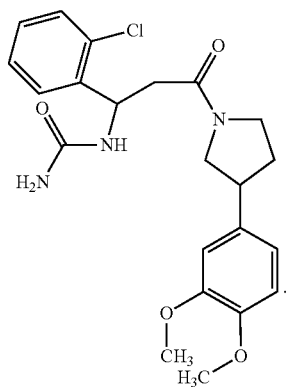

(X)

Some embodiments provide for combination therapy, such as FAK activation small molecules and immunotherapy (e.g., immunosuppressives; immunotherapy) and/or anti-ulcer therapy (e.g., anti-acid secretory agents). For example, oral administration, either by direct dosing or via an enteral release formulation, could be synergistic with conventional immunosuppressive therapy in IBD, enhancing quality of life at lower immunosuppressive dosing.

In the paradigmatic case of the patient whose Crohn's disease has flared, adding a parenteral drug that activates enterocytic FAK for three days during aggressive immunosuppression can make the difference between hospital discharge and surgery.

Pharmaceutical Compositions/Administration/Disorders

The present disclosure also contemplates pharmaceutical compositions comprising one or more compounds disclosed herein, one or more pharmaceutically acceptable carriers, diluents, excipients or combinations thereof. A "pharmaceutical composition" refers to a chemical or biological composition suitable for administration to a subject (e.g., mammal). Such compositions can be specifically formulated for administration via one or more of a number of routes, including but not limited to buccal, cutaneous, epicutaneous, epidural, infusion, inhalation, intraarterial, intracardial, intracerebroventricular, intradermal, intramuscular, intranasal, intraocular, intraperitoneal, intraspinal, intrathecal, intravenous, oral, parenteral, pulmonary, rectally via an enema or suppository, subcutaneous, subdermal, sublingual, transdermal, and transmucosal. In addition, administration can by means of capsule, drops, foams, gel, gum, injection, liquid, patch, pill, porous pouch, powder, tablet, or other suitable means of administration.

A "pharmaceutical excipient" or a "pharmaceutically acceptable excipient" comprises a carrier, sometimes a liquid, in which an active therapeutic agent is formulated. The excipient generally does not provide any pharmacological activity to the formulation, though it may provide chemical and/or biological stability, and release characteristics. Examples of suitable formulations can be found, for example, in Remington, The Science and Practice of Pharmacy, 20th Edition, (Gennaro, A. R., Chief Editor), Philadelphia College of Pharmacy and Science, 2000, which is incorporated by reference in its entirety.

As used herein "pharmaceutically acceptable carrier" or "excipient" includes any and all solvents, dispersion media, coatings, antibacterial and antifungal agents, isotonic and absorption delaying agents that are physiologically compatible. The carrier is suitable for, among other applications, parenteral administration. Alternatively, the carrier can be suitable for intravenous, intraperitoneal, intramuscular, sublingual, or oral administration. Pharmaceutically acceptable carriers include sterile aqueous solutions or dispersions and sterile powders for the extemporaneous preparation of sterile injectable solutions or dispersion. The use of such media and agents for pharmaceutically active substances is well known in the art. Except insofar as any conventional media or agent is incompatible with the active compound, use thereof in the pharmaceutical compositions is contemplated. Supplementary active compounds can also be incorporated into the compositions.

Pharmaceutical compositions can be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (e.g., glycerol, propylene glycol, and liquid polyethylene glycol), and suitable mixtures thereof. The proper fluidity can be maintained, for example, by the use of a coating such as lecithin, by the maintenance of the required particle size in the case of dispersion and by the use of surfactants.

In many cases, it will be preferable to include isotonic agents, for example, sugars, polyalcohols such as mannitol, sorbitol, or sodium chloride in the composition. Prolonged absorption of the injectable compositions can be brought about by including in the composition an agent which delays absorption, for example, monostearate salts and gelatin. Moreover, the compounds described herein can be formulated in a time release formulation, for example in a composition that includes a slow release polymer. The active compounds can be prepared with carriers that will protect the compound against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, polylactic acid and polylactic, polyglycolic copolymers (PLG). Many methods for the preparation of such formulations are known to those skilled in the art.

Oral forms of administration are also contemplated herein. The pharmaceutical compositions can be orally administered as a capsule (hard or soft), tablet (film coated, enteric coated or uncoated), powder or granules (coated or uncoated) or liquid (solution or suspension). The formulations can be conveniently prepared by any of the methods well-known in the art. The pharmaceutical compositions can include one or more suitable production aids or excipients including fillers, binders, disintegrants, lubricants, diluents, flow agents, buffering agents, moistening agents, preservatives, colorants, sweeteners, flavors, and pharmaceutically compatible carriers.

The compounds can be administered by a variety of dosage forms as known in the art. Any biologically-acceptable dosage form known to persons of ordinary skill in the art, and combinations thereof, are contemplated. Examples of such dosage forms include, without limitation, chewable tablets, quick dissolve tablets, effervescent tablets, reconstitutable powders, elixirs, liquids, solutions, suspensions, emulsions, tablets, multi-layer tablets, bi-layer tablets, capsules, soft gelatin capsules, hard gelatin capsules, caplets, lozenges, chewable lozenges, beads, powders, gum, granules, particles, microparticles, dispersible granules, cachets, douches, suppositories, creams, topicals, inhalants, aerosol inhalants, patches, particle inhalants, implants, depot implants, ingestibles, injectables (including subcutaneous, intramuscular, intravenous, and intradermal), infusions, and combinations thereof.

Other compounds which can be included by admixture are, for example, medically inert ingredients (e.g., solid and liquid diluent), such as lactose, dextrosesaccharose, cellulose, starch or calcium phosphate for tablets or capsules, olive oil or ethyl oleate for soft capsules and water or vegetable oil for suspensions or emulsions; lubricating agents such as silica, talc, stearic acid, magnesium or calcium stearate and/or polyethylene glycols; gelling agents such as colloidal clays; thickening agents such as gum tragacanth or sodium alginate, binding agents such as starches, arabic gums, gelatin, methylcellulose, carboxymethylcellulose or polyvinylpyrrolidone; disintegrating agents such as starch, alginic acid, alginates or sodium starch glycolate; effervescing mixtures; dyestuff; sweeteners; wetting agents such as lecithin, polysorbates or laurylsulphates; and other therapeutically acceptable accessory ingredients, such as humectants, preservatives, buffers and antioxidants, which are known additives for such formulations.

Liquid dispersions for oral administration can be syrups, emulsions, solutions, or suspensions. The syrups can contain as a carrier, for example, saccharose or saccharose with glycerol and/or mannitol and/or sorbitol. The suspensions and the emulsions can contain a carrier, for example a natural gum, agar, sodium alginate, pectin, methylcellulose, carboxymethylcellulose, or polyvinyl alcohol.

The amount of active compound in a therapeutic composition can vary according to factors such as the disease state, age, gender, weight, patient history, risk factors, predisposition to disease, administration route, pre-existing treatment regime (e.g., possible interactions with other medications), and weight of the individual. Dosage regimens can be adjusted to provide the optimum therapeutic response. For example, a single bolus can be administered, several divided doses can be administered over time, or the dose can be proportionally reduced or increased as indicated by the exigencies of therapeutic situation.

"Dosage unit form," as used herein, refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms are dictated by and can be directly dependent on the unique characteristics of the active compound and the particular therapeutic effect to be achieved, and the limitations inherent in the art of compounding such an active compound for the treatment of sensitivity in individuals. In therapeutic use for treatment of conditions in mammals (e.g., humans) for which the compounds disclosed herein, or an appropriate pharmaceutical composition thereof are effective, the compounds disclosed herein can be administered in an effective amount. The dosages as suitable for this disclosure can be a composition, a pharmaceutical composition or any other compositions described herein.

The dosage can be administered once, twice, thrice or four times a day, although more frequent dosing intervals are possible. The dosage can be administered every day, every 2 days, every 3 days, every 4 days, every 5 days, every 6 days, and/or every 7 days (once a week). The dosage can be administered daily for up to and including 30 days, preferably between 7-10 days. Or the dosage can be administered twice a day for 10 days. If the patient requires treatment for a chronic disease or condition, the dosage can be administered for as long as signs and/or symptoms persist. The patient may require "maintenance treatment" where the patient is receiving dosages every day for months, years, or the remainder of their lives. In addition, the composition can affect prophylaxis of recurring symptoms. For example, the dosage can be administered once or twice a day to prevent the onset of symptoms in patients at risk, especially for asymptomatic patients.

The compositions described herein can be administered in any of the following routes: buccal, epicutaneous, epidural, infusion, inhalation, intraarterial, intracardial, intracerebroventricular, intradermal, intramuscular, intranasal, intraocular, intraperitoneal, intraspinal, intrathecal, intravenous, oral, parenteral, pulmonary, rectally via an enema or suppository, subcutaneous, subdermal, sublingual, transdermal, and transmucosal. The administration can be local, where the composition is administered directly, close to, in the locality, near, at, about, or in the vicinity of, the site(s) of disease, e.g., inflammation, or systemic, wherein the composition is given to the patient and passes through the body widely, thereby reaching the site(s) of disease. Local administration can be administration to the cell, tissue, organ, and/or organ system, which encompasses and/or is affected by the disease, and/or where the disease signs and/or symptoms are active or are likely to occur. Administration can be topical with a local effect, composition is applied directly where its action is desired. Administration can be enteral wherein the desired effect is systemic (non-local), composition is given via the digestive tract. Administration can be parenteral, where the desired effect is systemic, composition is given by other routes than the digestive tract.

Also contemplated herein are compositions comprising a therapeutically effective amount of one or more compounds provided herein that are useful in a method for treating an epithelial disease, such as a gut disorder, including but not limited to Crohn's disease, celiac disease, peptic ulcer disease, IBD and/or ulcerative colitis, necrotizing enterocolitis (NEC), or loss of mucosal barrier, for example in illness that contributes to bacterial translocation and septic states, or to promote skin wound epithelialization, oral ulcer healing, or other epithelial wound healing disorders of skin or cornea (e.g., eczema, psoriasis, epithelial carcinoma, asthma and/or corneal abrasions).

The term "therapeutically effective amount" as used herein, refers to that amount of one or more compounds disclosed herein that elicits a biological or medicinal response in a tissue system, animal or human, that is being sought by a researcher, veterinarian, medical doctor or other clinician, which includes alleviation of the symptoms of the disease or disorder being treated. The therapeutically effective amount can be that which may treat or alleviate the disease or symptoms of the disease at a reasonable benefit/risk ratio applicable to any medical treatment. However, it is to be understood that the total daily usage of the compounds and compositions described herein can be decided by the attending physician within the scope of sound medical judgment. The specific therapeutically-effective dose level for any particular patient will depend upon a variety of factors, including the condition being treated and the severity of the condition; activity of the specific compound employed; the specific composition employed; the age, body weight, general health, gender and diet of the patient: the time of administration, route of administration, and rate of excretion of the specific compound employed; the duration of the treatment; drugs used in combination or coincidentally with the specific compound employed; and like factors well known to the researcher, veterinarian, medical doctor or other clinician. It is also appreciated that the therapeutically effective amount can be selected with reference to any toxicity, or other undesirable side effect, that might occur during administration of one or more of the compounds described herein.

Values expressed in a range format should be interpreted in a flexible manner to include not only the numerical values explicitly recited as the limits of the range, but also to include all the individual numerical values or sub-ranges encompassed within that range as if each numerical value and sub-range were explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z," unless indicated otherwise.

In this document, the terms "a," "an," or "the" are used to include one or more than one unless the context clearly dictates otherwise. The term "or" is used to refer to a nonexclusive "or" unless otherwise indicated. In addition, it is to be understood that the phraseology or terminology employed herein, and not otherwise defined, is for the purpose of description only and not of limitation. Any use of section headings is intended to aid reading of the document and is not to be interpreted as limiting. Further, information that is relevant to a section heading may occur within or outside of that particular section. Furthermore, all publications, patents, and patent documents referred to in this document are incorporated by reference herein in their entirety, as though individually incorporated by reference.

In the methods described herein, the steps can be carried out in any order without departing from the spirit of this disclosure, except when a temporal or operational sequence is explicitly recited. Furthermore, specified steps can be carried out concurrently unless explicit claim language recites that they be carried out separately. For example, a claimed step of doing X and a claimed step of doing Y can be conducted simultaneously within a single operation, and the resulting process will fall within the literal scope of the claimed process.

The term "about" as used herein can allow for a degree of variability in a value or range, for example, within 10%, within 5%, or within 1% of a stated value or of a stated limit of a range.

The term "organic group" as used herein refers to any carbon-containing functional group. Examples can include an oxygen-containing group such as an alkoxy group, aralkyloxy group, a carboxyl group including a carboxylic acid, carboxylate, and a carboxylate ester; a sulfur-containing group such as an alkyl and aryl sulfide group; and other heteroatom-containing groups. Non-limiting examples of organic groups include OR, OOR, OC(O)N(R)$_2$, CN, CF$_3$, OCF$_3$, R, C(O), methylenedioxy, ethylenedioxy, N(R)$_2$, SR, SOR, SO$_2$R, SO$_2$N(R)$_2$, SO$_3$R, C(O)R, C(O)C(O)R, C(O)CH$_2$C(O)R, C(S)R, C(O)OR, OC(O)R, C(O)N(R)$_2$, OC(O)N(R)$_2$, C(S)N(R)$_2$, (CH$_2$)$_{0-2}$N(R)C(O)R, (CH$_2$)$_{0-2}$N(R)N(R)$_2$, N(R)N(R)C(O)R, N(R)N(R)C(O)OR, N(R)N(R)CON(R)$_2$, N(R)SO$_2$R, N(R)SO$_2$N(R)$_2$, N(R)C(O)OR, N(R)C(O)R, N(R)C(S)R, N(R)C(O)N(R)$_2$, N(R)C(S)N(R)$_2$, N(COR)COR, N(OR)R, C(=NH)N(R)$_2$, C(O)N(OR)R, C(=NOR)R, and substituted or unsubstituted (C$_1$-C$_{100}$)hydrocarbyl, wherein R can be hydrogen (in examples that include other carbon atoms) or a carbon-based moiety, and wherein the carbon-based moiety can be substituted or unsubstituted.

The term "substituted" as used herein in conjunction with a molecule or an organic group as defined herein refers to the state in which one or more hydrogen atoms contained therein are replaced by one or more non-hydrogen atoms. The term "functional group" or "substituent" as used herein refers to a group that can be or is substituted onto a molecule or onto an organic group. Examples of substituents or functional groups include, but are not limited to, a halogen (e.g., F, Cl, Br, and I); an oxygen atom in groups such as hydroxy groups, alkoxy groups, carboxyl groups including carboxylic acids, carboxylates, and carboxylate esters; a sulfur atom in groups such as thiol groups, alkyl and aryl sulfide groups, sulfoxide groups, sulfone groups, sulfonyl groups, and sulfonamide groups; a nitrogen atom in groups such as amines, hydroxyamines, nitriles, nitro groups, N-oxides, hydrazides, azides, and enamines; and other heteroatoms in various other groups. Non-limiting examples of substituents that can be bonded to a substituted carbon (or other) atom include F, Cl, Br, I, OR, OC(O)N(R)$_2$, CN, NO, NO$_2$, ONO$_2$, azido, CF$_3$, OCF$_3$, R, O (oxo), S (thiono), C(O), S(O), methylenedioxy, ethylenedioxy, N(R)$_2$, SR, SOR, SO$_2$R, SO$_2$N(R)$_2$, SO$_3$R, C(O)R, C(O)C(O)R, C(O)CH$_2$C(O)R, C(S)R, C(O)OR, OC(O)R, C(O)N(R)$_2$, OC(O)N(R)$_2$, C(S)N(R)$_2$, (CH$_2$)$_{0-2}$N(R)C(O)R, (CH$_2$)$_{0-2}$N(R)N(R)$_2$, N(R)N(R)C(O)R, N(R)N(R)C(O)OR, N(R)N(R)CON(R)$_2$, N(R)SO$_2$R, N(R)SO$_2$N(R)$_2$, N(R)C(O)OR, N(R)C(O)R, N(R)C(S)R, N(R)C(O)N(R)$_2$, N(R)C(S)N(R)$_2$, N(COR)COR, N(OR)R, C(=NH)N(R)$_2$, C(O)N(OR)R, and C(=NOR)R, wherein R can be hydrogen or a carbon-based moiety; for example, R can be hydrogen, (C$_1$-C$_{100}$)hydrocarbyl, alkyl, acyl, cycloalkyl, aryl; or wherein two R groups bonded to a nitrogen atom or to adjacent nitrogen atoms can together with the nitrogen atom or atoms form a heterocyclyl.

The term "alkyl" as used herein refers to straight chain and branched alkyl groups and cycloalkyl groups having from 1 to 40 carbon atoms, 1 to about 20 carbon atoms, 1 to 12 carbons or, in some embodiments, from 1 to 8 carbon atoms. Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, t-butyl, neopentyl, isopentyl, and 2,2-dimethylpropyl groups. As used herein, the term "alkyl" encompasses n-alkyl, isoalkyl, and anteisoalkyl groups as well as other branched chain forms of alkyl. Representative substituted alkyl groups can be substituted one or more times with any of the groups listed herein, for example, amino, hydroxy, cyano, carboxy, nitro, thio, alkoxy, and halogen groups.

The term "alkenyl" as used herein refers to straight and branched chain and cyclic alkyl groups as defined herein, except that at least one double bond exists between two carbon atoms. Thus, alkenyl groups have from 2 to 40 carbon atoms, or 2 to about 20 carbon atoms, or 2 to 12 carbon atoms or, in some embodiments, from 2 to 8 carbon atoms. Examples include, but are not limited to vinyl, —CH=CH(CH$_3$), —CH=C(CH$_3$)$_2$, —C(CH$_3$)=CH$_2$, —C(CH$_3$)=CH(CH$_3$), —C(CH$_2$CH$_3$)=CH$_2$, cyclohexenyl, cyclopentenyl, cyclohexadienyl, butadienyl, pentadienyl, and hexadienyl among others.

The term "alkynyl" as used herein refers to straight and branched chain alkyl groups, except that at least one triple bond exists between two carbon atoms. Thus, alkynyl groups have from 2 to 40 carbon atoms, 2 to about 20 carbon atoms, or from 2 to 12 carbons or, in some embodiments, from 2 to 8 carbon atoms. Examples include, but are not limited to —C≡CH, —C≡C(CH$_3$), —C≡C(CH$_2$CH$_3$), —CH$_2$C≡CH, —CH$_2$C≡C(CH$_3$), and —CH$_2$C≡C(CH$_2$CH$_3$) among others.

The term "acyl" as used herein refers to a group containing a carbonyl moiety wherein the group is bonded via the carbonyl carbon atom. The carbonyl carbon atom is bonded to a hydrogen forming a "formyl" group or is bonded to another carbon atom, which can be part of an alkyl, aryl, aralkyl cycloalkyl, or cycloalkylalkyl. An acyl group can include 0 to about 12, 0 to about 20, or 0 to about 40 additional carbon atoms bonded to the carbonyl group. An acyl group can include double or triple bonds within the meaning herein. An acryloyl group is an example of an acyl group. An acyl group can also include heteroatoms within the meaning herein. A nicotinoyl group (pyridyl-3-carbonyl) is an example of an acyl group within the meaning herein. Other examples include acetyl, benzoyl, phenylacetyl, pyridylacetyl, cinnamoyl, and acryloyl groups and the like. When the group containing the carbon atom that is bonded to the carbonyl carbon atom contains a halogen, the group is termed a "haloacyl" group. An example is a trifluoroacetyl group.

The term "cycloalkyl" as used herein refers to cyclic alkyl groups such as, but not limited to, cyclopropyl, cyclobutyl, cyclopentyl, cyclohexyl, cycloheptyl, and cyclooctyl groups. In some embodiments, the cycloalkyl group can have 3 to about 8-12 ring members, whereas in other embodiments the number of ring carbon atoms range from 3 to 4, 5, 6, or 7. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like. Cycloalkyl groups also include rings that are substituted with straight or branched chain alkyl groups as defined herein. Representative substituted cycloalkyl groups can be mono-substituted or substituted more than once, such as, but not limited to, 2,2-, 2,3-, 2,4-2,5- or 2,6-disubstituted cyclohexyl groups or mono-, di- or tri-substituted norbornyl or cycloheptyl groups, which can be substituted with, for example, amino, hydroxy, cyano, carboxy, nitro, thio, alkoxy, and halogen groups. The term "cycloalkenyl" alone or in combination denotes a cyclic alkenyl group.

The term "aryl" as used herein refers to cyclic aromatic hydrocarbon groups that do not contain heteroatoms in the ring. Thus, aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain about 6 to about 14 carbons in the ring portions of the groups. Aryl groups can be unsubstituted or substituted, as defined herein. Representative substituted aryl groups can be mono-substituted or substituted more than once, such as, but not limited to, a phenyl group substituted at any one or more of 2-, 3-, 4-, 5-, or 6-positions of the phenyl ring, or a naphthyl group substituted at any one or more of 2- to 8-positions thereof.

The term "alkoxy" as used herein refers to an oxygen atom connected to an alkyl group, including a cycloalkyl group, as are defined herein. Examples of linear alkoxy groups include but are not limited to methoxy, ethoxy, propoxy, butoxy, pentyloxy, hexyloxy, and the like. Examples of branched alkoxy include but are not limited to isopropoxy, sec-butoxy, tert-butoxy, isopentyloxy, isohexyloxy, and the like. Examples of cyclic alkoxy include but are not limited to cyclopropyloxy, cyclobutyloxy, cyclopentyloxy, cyclohexyloxy, and the like. An alkoxy group can include about 1 to about 12, about 1 to about 20, or about 1 to about 40 carbon atoms bonded to the oxygen atom, and can further include double or triple bonds, and can also include heteroatoms. For example, an allyloxy group or a methoxyethoxy group is also an alkoxy group within the meaning herein, as is a methylenedioxy group in a context where two adjacent atoms of a structure are substituted therewith.

The term "amine" as used herein refers to primary, secondary, and tertiary amines having, e.g., the formula N(group)$_3$ wherein each group can independently be H or non-H, such as alkyl, aryl, and the like. Amines include but are not limited to R—NH$_2$, for example, alkylamines, arylamines, alkylarylamines; R$_2$NH wherein each R is independently selected, such as dialkylamines, diarylamines, aralkylamines, and the like; and R$_3$N wherein each R is independently selected, such as trialkylamines, dialkylarylamines, alkyldiarylamines, triarylamines, and the like. The term "amine" also includes ammonium ions as used herein.

The term "haloalkyl" group, as used herein, includes mono-halo alkyl groups, poly-halo alkyl groups wherein all halo atoms can be the same or different, and per-halo alkyl groups, wherein all hydrogen atoms are replaced by halogen atoms, such as fluoro. Examples of haloalkyl include trifluoromethyl, 1,1-dichloroethyl, 1,2-dichloroethyl, 1,3-dibromo-3,3-difluoropropyl, perfluorobutyl, and the like.

As used herein, the term "hydrocarbyl" refers to a functional group derived from a straight chain, branched, or cyclic hydrocarbon, and can be alkyl, alkenyl, alkynyl, aryl, cycloalkyl, acyl, or any combination thereof. Hydrocarbyl groups can be shown as $(C_a$-$C_b)$hydrocarbyl, wherein a and b are integers and mean having any of a to b number of carbon atoms. For example, $(C_1$-$C_4)$hydrocarbyl means the hydrocarbyl group can be methyl ($C_1$), ethyl ($C_2$), propyl ($C_3$), or butyl ($C_4$), and $(C_0$-$C_b)$hydrocarbyl means in certain embodiments there is no hydrocarbyl group.

As used herein, the term "salts" and "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. Pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

Pharmaceutically acceptable salts can be synthesized from the parent compound which contains a basic or acidic moiety by conventional chemical methods. In some instances, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, the disclosure of which is hereby incorporated by reference.

The term "solvate" means a compound, or a salt thereof, that further includes a stoichiometric or non-stoichiometric amount of solvent bound by non-covalent intermolecular forces. Where the solvent is water, the solvate is a hydrate.

Although parenteral dosing would be appropriate for acute treatment, oral administration would clearly be of value in the chronic setting when such molecules are applied to chronic disorders of mucosal healing such as IBD or celiac disease in the outpatient setting. Luminal administration of these agents would be clinically advantageous in outpatients, either orally or rectally for proctitis, as is now done with Proctofoam enemas.

Screening Additional Compounds

Potential drug candidates can be screened/tested in a biochemical assay to assess the potency to stimulate Caco-2 (by Western blotting for FAK-397) and HIEC-6 FAK activation (by a commercially available ELISA for FAK-Y-397). To validate their activity, the assay will be performed by two different techniques in two different cell lines.

Successful molecules will be further confirmed that Caco-2 monolayer wound closure is enhanced in parallel studies since HIEC-6 cells don't form tight monolayers or display epithelial sheet migration. This longer experiment (24 hours vs. 1 hour) will also offer an initial screen for unexpected potent cytotoxicity. The most successful molecules will be submitted for ADMET assays (including metabolic stability, solubility (pH 7.4), Caco-2 (permeability) and log D determination).

Further assays to screen compounds can include the following:

The specificity of candidate molecules for the activation of FAK vs. other tyrosine kinases can be determined (A). Further, whether they modulate relevant tyrosine phosphatases can be assessed (B).

A. Tyrosine Kinase Studies i. Members of the Jak family of tyrosine kinases, kinases such as Src, Pyk2, Jak1 and/or Jak2 are tyrosine kinases of the class that like FAK are not membrane-bound. Caco-2 cells will be treated with potential candidate compounds (10 nM) or relevant vehicle (DMSO) control. Activation of FAK, Src, and Jak1 can be assessed by Western blotting with phosphospecific antibodies to FAK-Y-397, Src-Y-419, and Jak1-Y1034/1035 that indicate the activation of these proteins (25, 26).

ii. If Src or Jak1 phosphorylation appears increased by experiment Ai above, then true activation by direct action, indirect activation consequent to FAK activation, or some other phosphorylation event will be distinguished/determined. To determine this in vitro kinase assays can be performed using commercially available purified human FAK for the compound(s) at 0, 1, 10, 30, 70, 100 pM and compare the effects to the effects of similar concentrations on Src and Jak1 activity using a purified synthetic substrate.

iii. If Src or Jak1 phosphorylation is increased in Ai, but in vitro kinase activity is not changed in Aii, then the possibility that the effect in intact cells represents a consequence of FAK activation by these molecules will be considered and will be tested, for example, by simultaneously using siRNA to knock down FAK during treatment with the compounds (e.g., FAK activators) and then investigate Src or Jak1 phosphorylation as appropriate.

B. Tyrosine Phosphatase Studies a. D3 does not activate SHP2. Via a similar and published (24) assay kit (Anaspec #AS-7100), the effects of D3 and/or other compounds/candidate FAK activators will be tested on PTP1B and PTP-PEST tyrosine phosphatase activity at concentrations 0.1×, 1×, 10×, and 100× the lowest concentration required to activate FAK within intact Caco-2 cells.

b. FAK will be immuno-precipitated and Western blot for SHP2, PTP-PEST, and PTP1B after treatment of Caco-2 cells with D3 and/or other compounds/candidate FAK activators or a DMSO vehicle control.

EXAMPLES

The following examples are offered by way of illustration. But the present disclosure is not limited to the examples given herein.

Introduction

IBD (including Crohn's disease and ulcerative colitis) is a chronic GI idiopathic inflammatory disorder afflicting over one million Americans (1). Inadequate mucosal healing causes many common diseases in addition to IBD. Those include peptic ulcer, celiac disease, NEC, and the mucosal barrier failure in critical illness that leads to sepsis. Failure to heal a mucosal injury can result in loss of bowel or even life. One paradigmatic example would be the patient hospitalized with an acute flare of Crohn's disease, who is managed medically for a few days with even more aggressive immunosuppression and then taken to surgery if that fails. This not only subjects the patient to risky surgery with attendant pain and morbidity, but irretrievably reduces the amount of small intestine available for nutrient absorption. This may ultimately lead to short gut syndrome if subsequent disease flares require repeated resections. Healing represents an equilibrium between the processes that injure the bowel mucosa (inflammation, ischemia, and luminal agents) and the epithelial sheet migration and proliferation required to resurface injured gut. However, virtually all current approaches to managing mucosal injury focus on reducing injury (e.g., immunosuppressives, anti-acid agents). The only therapeutic that may promote healing is sucralfate, which some have hypothesized to bind luminal growth factors and plaster them across peptic ulcers (8).

FAK activation plays a role in mucosal healing (9). Therefore, developing a new therapy for GI mucosal healing is an important unmet medical need affecting millions of patients nationally and worldwide. Provided herein are FAK-activating agents compounds that can specifically promote epithelial restitution and mucosal healing, offering the ability to heal mucosal injury either without or in synergistic combination with immunosuppressives. In the paradigmatic case of the patient whose Crohn's disease has flared, adding a parenteral drug that activates enterocytic FAK for three days during aggressive immunosuppression can make the difference between hospital discharge and surgery.

This novel approach builds upon the observation that certain small molecules that mimic the tertiary structure of one subdomain of FAK result in FAK activation (7). No known therapeutic agent specifically activates FAK, although diverse growth factors and cytokines activate FAK along with many other kinases. No currently known agent directly and specifically promotes intestinal epithelial sheet migration and mucosal healing except, as noted above, for the idea that sucralfate promotes peptic ulcer healing not only by "bandaging" ulcers, but by creating a poultice with luminal growth factors (8). Tyrosine phosphatase inhibitors are known. For instance, a SHP-2 inhibitor is in clinical trials for cancer (10). However, the molecules provided herein are not tyrosine phosphatase inhibitors (which would activate many kinases other than FAK) but promote the activation of FAK itself. (Preliminary data shows neither Src nor Pyk2 is activated, neither SHP-2 activity nor PTP-1B-FAK association are inhibited, and a PTP-PEST inhibitor does not block the effect.) Such selectivity permits substantially higher doses with less toxicity.

Example 1

Increased FAK Phosphorylation/Activation

Results/Discussion

FAK-Y397 western blotting: For studies of FAK activation, cells were maintained at ambient or increased pressure in bacteriologic plastic dishes pacificated with heat-inactivated bovine serum albumin to prevent adhesion and avoid adhesion-associated background FAK activation. Cells were lysed in lysis buffer, resolved by 10% SDS-PAGE, transferred to nitrocellulose and blotted with antibody to Tyr-397-phosphorylated FAK (Rabbit monoclonal antibody, ab81298, Abcam, USA) and anti-rabbit 680 (LI-COR, USA), before quantitation using Kodak Scientific Imaging Systems 1D, V.3.5.4 within the linear range of exposure (Oncotarget 2017). Total FAK (Primary antibody: Anti- FAK, clone 4.47 Merck, Germany and secondary antibody: anti-mouse 800, LI-COR, USA) served as a protein loading control.

Four molecules, ZINC31501681 (Compound 1), ZINC58264388 (Compound 2), ZINC40099027 (Compound 3), and ZINC25613745 (Compound 4) were each found to increase basal FAK-Tyr-397 phosphorylation even at ambient pressure at varying concentrations Studies show that study, for example Compound 1, results in an increase in phosphorylated FAK at concentrations of 100 pM, 10 pM, and 1 pM (and concentrations ranging from 10 pM to 1 nM, and 1-100 µM). No significant increase in FAK-Tyr-397 phosphorylation was seen with pressure. Increased extracellular pressure also activates FAK phosphorylation, as a positive control. Compound 2 provided modest FAK activation at concentrations of 10 and 100 nM. Compound 3 provided activation at concentrations ranging from 10 pM to 1 nM. Compounds 2 and 3 have demonstrated FAK activation at 1 nM.

FAKs Role in Mucosal Healing.

Decreased FAK activation has been shown in migrating intestinal epithelial cells in vitro; decreased epithelial sheet migration occurs when FAK is reduced in vitro; and decreased FAK activation has been shown at the migrating edge of human mucosal ulcers (Yu C F, Sanders M A, Basson M D. Human Caco-2 motility redistributes FAK and paxillin and activates p38 MAPK in a matrix-dependent manner. Am J Physiol. 279:G952-G966, 2000; Basson M D, Sanders M A, Gomez R, Hatfield J, VanderHeide R, Thamilselvan V, Zhang J, Walsh M F. Focal adhesion kinase protein levels in gut epithelial motility. Am J Physiol. 291(3):G491-9, 2006). Here you have citations in text again, while above you have them as #'s.

As FAK activation drives epithelial sheet migration, it follows that FAK activating compounds will enhance mucosal wound healing.

Several studies were performed on Caco-2 cell monolayers on Collagen-I. Cell migration at 24 hours was demonstrated microscopically for Compound 1 at 300 µM. Increased wound closure rates were observed for each of Compounds 1 (1 µM), 2 (100 µM), 3 (10 nM), and 4 (10 nM), and for Compound 1 (300 µM) and Compound 3 (100 µM and 10 nM). Pooled data for Compound 3 (10 nM) also reflects increased wound closure.

Neither Compound 1 nor Compound 3 stimulated Caco-2 cell proliferation, so the wound closure effect appears to be due to migration rather than reflecting increased cell numbers.

An in vivo study was conducted utilizing C57BL6 Male/Female>8-week-old mice. During laparotomy under anesthesia, a filter paper soaked with 75% Acetic Acid was applied to ileal serosa for 15 seconds, a technique that produces reproducible mucosal ulcers at day 4 without opening the bowel. Flanigan T L et al., Am J Surg. 2008 November; 196(5): 683-689. doi:10.1016/j.amjsurg.2008.07.016.

At 1 day after ulcerogenesis, an intraperitoneal (IP) administration of Q6H-DMSO (2.4 ul+97.6 ul saline) was performed in a control sample, along with an IP injection of Q6H—Compound 3 (10 ug/ul) (2.4 ul+97.6 ul saline) in a test sample.

At 4 days after ulcerogenesis (day 3 after starting administration), the ulcer area was measured in each. The observed ulcer area and corresponding wound closure rate in vivo further evidences the effect of Compound 3.

An assessment of postoperative body weight was made to demonstrate that although all mice lost weight because of the surgical procedure and ulcer creation, the mice exposed to Compound 3 did not display further weight loss as evidence.

Serum concentration levels of Compound 3 were also measured in order to assess metabolism.

Data illustrates a FAK inhibitor (PF573228) that blocks ATP binding to FAK (a precondition for FAK autophosphorylation) and inhibits basal FAK autophosphorylation but does not prevent Compound 3 from increasing FAK autophosphorylation. This suggests that Compound 3 may act to block FAK dephosphorylation rather than directly stimulating FAK phosphorylation.

Data also show that the same FAK inhibitor reduces basal rates of wound healing in vitro and prevents the stimulation of wound healing by Compound 3. In light of this and the previous data, these results suggest that Compound 3 does act via its effect on FAK, but that PF-573228 has reduced FAK activation so much that even with the small increase in FAK activity engendered by the Compound 3 in the setting of PF-573228 treatment, there is still insufficient FAK activity to promote wound healing.

Further data confirms that compound 4 can activate FAK at a concentration of 10 nM (no change was observed at 1 nM). This is consistent with the previous observations that Compound 4, at the higher concentration, can promote Caco-2 monolayer wound healing in vitro as well.

Clauses

Clause 1. A method of activating focal adhesion kinase phosphorylation in eukaryotic cells, comprising the step of administering an effective amount of a compound selected from the group consisting of N-[(1S)-3-oxo-1-phenyl-3-[(2S)-2-([1,2,4]triazolo[4,3-a]pyridin-3-yl)pyrrolidin-1-yl]propyl]benzamide, [(1S)-3-[(2S)-2-(2-methylphenyl)pyrrolidin-1-yl]-3-oxo-1-thiophen-2-ylpropyl]urea, 2-(4-methoxyphenyl)-N-[2-(morpholin-4-yl)-5-(trifluoromethyl)phenyl]pyrrolidine-1-carboxamide, and 1-(2-chlorophenyl)-3-[2-(3,4-dimethoxyphenyl)pyrrolidin-1-yl]-3-oxopropylurea.

Clause 2. A method of treating an epithelial disease, comprising the step of administering to a patient an effective amount of a compound selected from the group consisting of N-[(1S)-3-oxo-1-phenyl-3-[(2S)-2-([1,2,4]triazolo[4,3-a]pyridin-3-yl)pyrrolidin-1-yl]propyl]benzamide, [(1S)-3-[(2S)-2-(2-methylphenyl)pyrrolidin-1-yl]-3-oxo-1-thiophen-2-ylpropyl]urea, 2-(4-methoxyphenyl)-N-[2-(morpholin-4-yl)-5-(trifluoromethyl)phenyl]pyrrolidine-1-carboxamide, and 1-(2-chlorophenyl)-3-[2-(3,4-dimethoxyphenyl)pyrrolidin-1-yl]-3-oxopropylurea.

Clause 3. The method of clause 2 wherein the route of administration is intraperitoneal.

Clause 4. The method of clause 2 wherein the route of administration is intravenous.

Clause 5. The method of clause 2 wherein the route of administration is oral.

Clause 6. The method of clause 2 wherein the route of administration is rectal.

Clause 7. The method of clause 2 wherein the route of administration is nasogastric tubing.

Clause 8. The method of clause 2 wherein the route of administration is enteric tubing.

Clause 9. The method of clause 2 wherein the epithelial disease is a gut disorder.

Clause 10. The method of clause 9 wherein the gut disorder is Crohn's disease.

Clause 11. The method of clause 9 wherein the gut disorder is peptic ulcer disease.

Clause 12. The method of clause 9 wherein the gut disorder is ulcerative colitis.

Example 2

Drug design, synthesis, characterization and optimization

Introduction

The data demonstrate that compound D3 (FIG. 1A) is a potent relatively non-toxic stimulator of wound healing in vitro and in vivo, activating FAK at 10 nM with at least 100× specificity vs. the most closely related kinase Pyk2. Related compounds 100× more potent have also been identified.

Results and Discussion

FAK activation begins with a conformational change that releases the FAK kinase domain from binding to the (inhibitory) FAK FERM domain. This frees the FAK kinase domain to auto-phosphorylate FAK at Tyr-397 (14). More recently, FAK-FAK dimerization via the FERM domain and FAT-FERM domain interaction has been proposed to induce a similar conformational change to allow FAK to auto-phosphorylate (15.) In either event, this initial Tyr-397 phosphorylation is typically used as a marker of FAK activation. It invokes further conformational changes that permit further activation of FAK by other kinases such as Src (16).

Figure 1B:
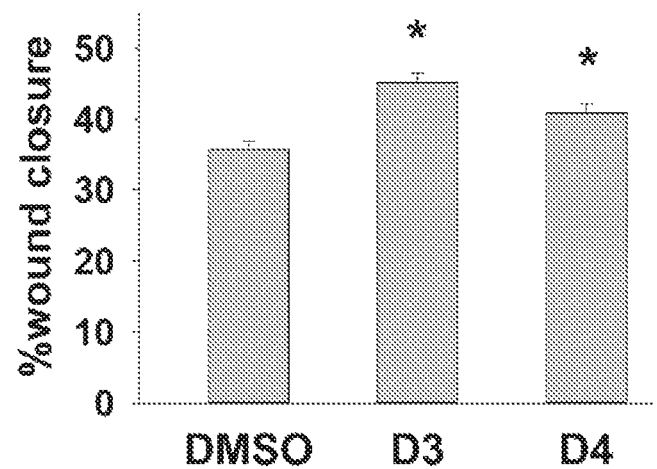
FIG. 1B depicts that D3 and D4 at 10 nM accelerate the closure of circular wounds in Caco-2 monolayers on collagen I (*$p<0.05$, $n=24$ pooled from 3 separate studies).

Molecules resembling the actual FAK sequence activated FAK and stimulated adhesiveness. Since FAK activation plays a role in epithelial restitution (5, 6, 9, 22), it was tested whether such molecules at 10 nM might not only activate FAK (FIG. 1A) but also promote epithelial monolayer wound closure (FIG. 1B). The two most potent of these compounds are termed D3 and D4.

D3: ZINC40099027 (2-(4-methoxyphenyl)-N-[2-(morpholin-4-yl)-5-(trifluoromethyl)phenyl]pyrrolidine-1-carboxamide)

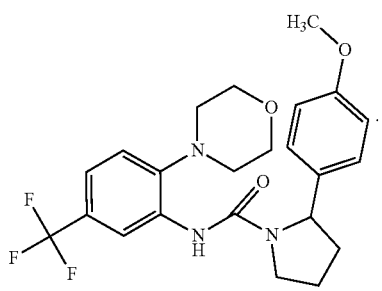 [SMILES: COc1ccc(C2CCCN2C(=O)Nc2cc(C(F)(F)F)ccc2N2CCOCC2)cc1]

D4: ZINC25613745 (1-(2-chlorophenyl)-3-[2-(3,4-dimethoxyphenyl)pyrrolidin-1-yl]-3-oxopropylurea)

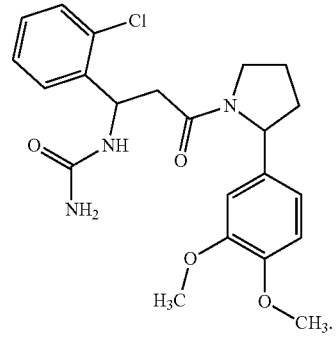 [SMILES: COc1ccc(C2CCCN2C(=O)CC(NC(N)=O)c2ccccc2Cl)cc1OC]

Figure 2A:
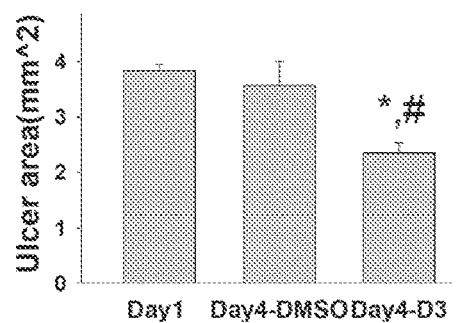
FIG. 2A is a bar graph depicting data showing that D3 reduces ileal ulcer area after topical serosal acetic acid application in mice at day zero, which causes a reproducible ulcer at day 1, and then, following day 1, after 3 subsequent days of every 6-hour IP injection of DMSO vehicle or D3 (900 ug/kg), ($n=8$, *$p<0.05$ vs. day 1, *$p<0.05$ vs DMSO).
Figure 2B:
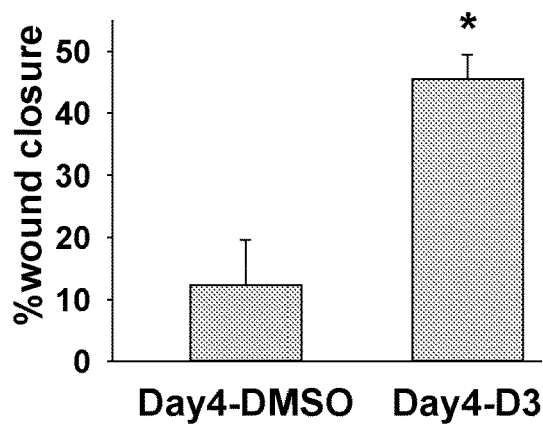
FIG. 2B is a bar graph depicting data showing that D3 stimulates ulcer healing. Data in FIG. 2A recalculated as % wound closure between day 1 and day 4 after every 6-hour IP injection of DMSO vehicle or D3 ($n=8$).
Figure 2C:
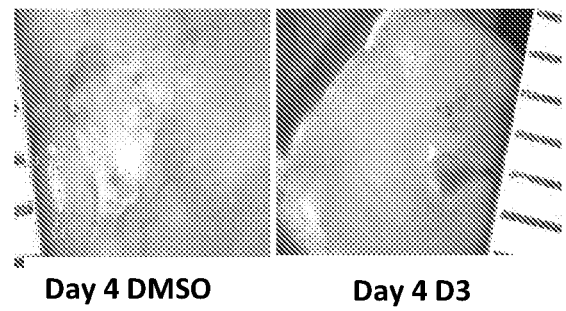
FIG. 2C demonstrates that typical ulcers appear smaller 4 days after serosal acetic acid induction and treatment with D3 vs DMSO vehicle (both photographed at same magnification; scale divisions=1 mm).
Figure 2D:
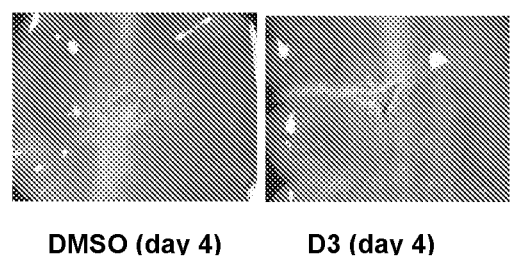
FIG. 2D demonstrates that D3 treatment markedly decreases total small bowel ulcer area over 4 days after indomethacin 15 mg/kg subQ. Typical ulcers are shown (photographed at same mag, but 1.6× those in FIG. 2C) together with the graph of total ulcer area ($n=20$, *$p<0.05$).
Figure 2D:
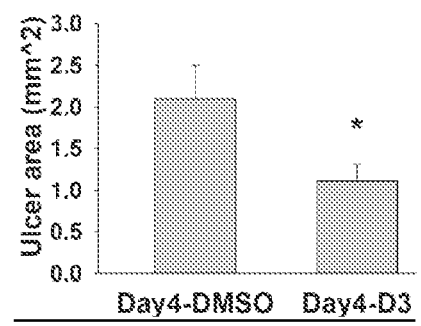
Figure 3:
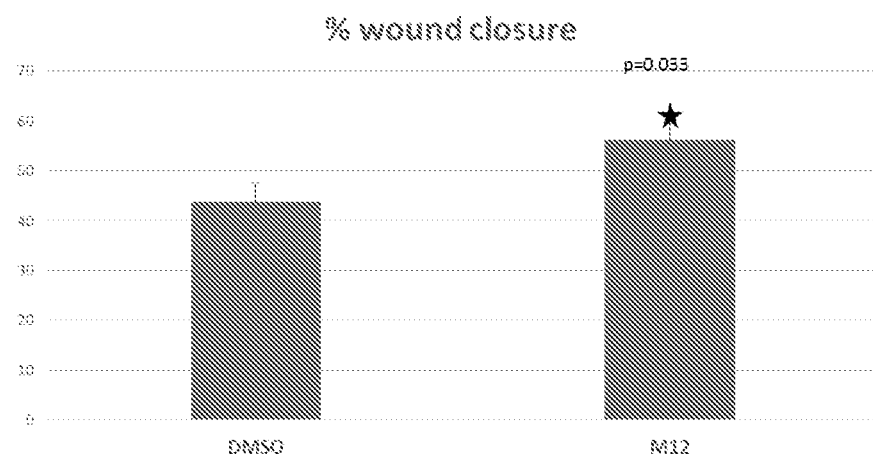
FIG. 3 is a bar graph depicting data that demonstrates that M12 stimulates monolayer wound closure at 10 nM.

While the magnitude of these effects may seem modest, even a small acceleration of mucosal healing can tip the equilibrium between continued injury and reconstitution of an intact mucosal barrier that resists injury (12, 23). D3 substantially accelerates healing in vivo (FIGS. 2B and 2D).

Figure 1E:
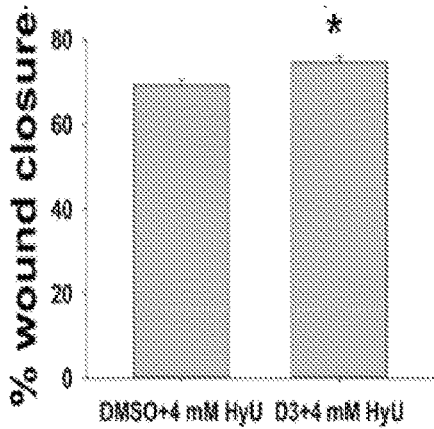
FIG. 1E depicts blockade of FAK with FAK inhibitor PF-573328 (10 uM) prevents D3 stimulation of wound closure.
Figure 1E:
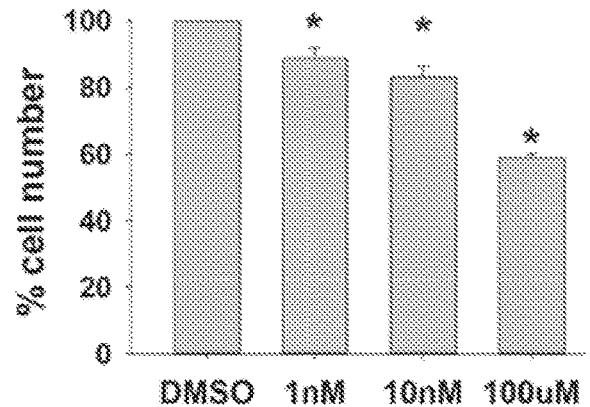
Figure 1E:
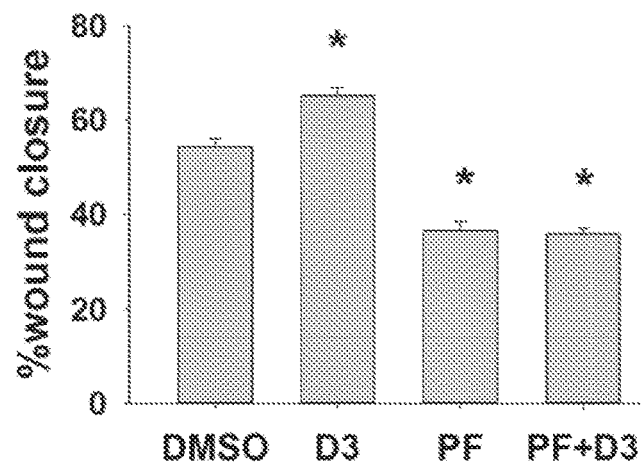

To demonstrate that the faster wound closure reflected cell migration (not proliferation), it demonstrated that D3 stimulates wound closure even when proliferation is blocked by 4 mM hydroxyurea (24) (FIG. 1C). It was also confirmed that cell number did not increase after 48 hours of D3 treatment (FIG. 1D). The FAK inhibitor PF-573328 (10 μM) prevented D3 stimulation of monolayer wound closure (FIG. 1E), consistent with the belief that stimulation of migration involves FAK, not an off-target side effect.

Figure 1M:
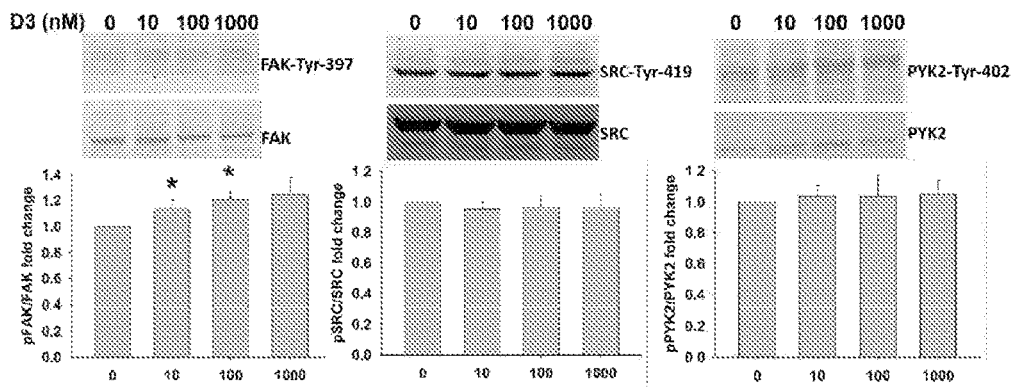
FIG. 1M demonstrates that D3 (10-1000 nM) dose dependently activates FAK, but D3 does not affect the kinase Pyk2 (also called FAK2) or the non-receptor tyrosine kinase Src that colocalizes with FAK in focal adhesion complexes even at 1000 nm.

Further studies demonstrated that the non-specific tyrosine kinase inhibitor genistein does not block D3 induction of FAK phosphorylation (FIG. 1F), suggesting that D3 does not activate FAK via an upstream kinase. The possibility that D3 inhibits one of the 3 tyrosine phosphatases that inactivate FAK was also investigated. D3 does not alter SHP2 activity in vitro (FIG. 1G) and does not change FAK-PTPB association by co-precipitation (FIG. 1H). PTP-PEST inhibition does not prevent D3 induction of FAK-Y-397 (FIG. 1I). Taken together, these findings demonstrate that these molecules do not act on an upstream kinase or a downstream phosphatase, but on FAK itself. With regards to selectivity, it was also determined that D3 does not activate Pyk2 or Src at 100× greater than the therapeutic threshold (FIG. 1M). Pyk2 is the tyrosine kinase most like FAK. Src and Jak1 are prototypical other tyrosine kinases that like FAK are not membrane-bound.

2-(4-methoxyphenyl)-N-(2-morpholino-5-(trifluoromethyl)phenyl)pyrrolidine-1-carboxamide (D3) was subjected to structure-activity relationship by commerce evaluation. Twelve compounds with high structural similarity and suitable in silico predicted drug-like properties were acquired and tested in vitro. The structures and physicochemical and other predicted properties computed using industry-standard Schrödinger software for successful compounds are represented in Table 1 below.

TABLE 1

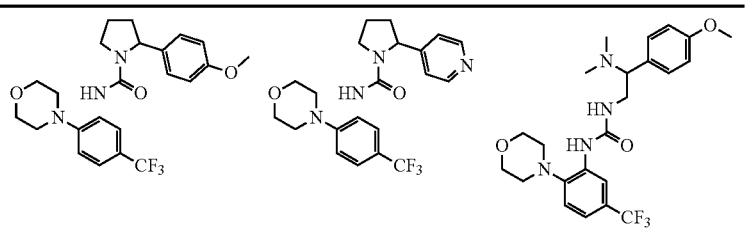

| Compound ID | | D3 | M3 | M6 |
|---|---|---|---|---|
| CAS | | | 1301763-47-2 | 1371916-00-5 |
| Calculated Properties (QikProp v.5.5) | | | | |
| MW | g/mol | 449.472 | 420.434 | 466.502 |
| Aqueous solubility | logS | −7.09 | −6.217 | −4.957 |
| Octanol/water clogP | logP | 5.242 | 4.202 | 4.071 |
| PSA | A | 49.474 | 54.409 | 66.915 |
| hERG | logIC$_{50}$ | −4.168 | 4.077 | −5.037 |
| Serum protein binding | logK | 0.723 | 0.382 | 0.333 |
| Caco-2 permeability | nm/sec | 6025 | 3156 | 691 |
| MDCK permeability | nm/sec | 10000M | 9502 | 2652M |
| Number of primary metabolites | | 4 | 5 | 5 |
| Rotatable bonds | | 2 | 1 | 6 |
| Human Oral Absorption | | low | low | high |

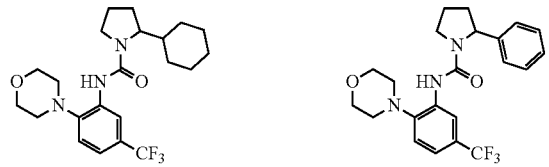

| Compound ID | | M11 | M12 |
|---|---|---|---|
| CAS | | 1388549-34-5 | N/A |
| Calculated Properties (QikProp v.5.5) | | | |
| MW | g/mol | 425.493 | 419.446 |
| Aqueous solubility | logS | −7.458 | −6.890 |
| Octanol/water clogP | logP | 5.319 | 5.151 |
| PSA | A | 39.608 | 41.501 |
| hERG | logIC$_{50}$ | −3.637 | −4.270 |
| Serum protein binding | logK | 0.870 | 0.721 |
| Caco-2 permeability | nm/sec | 6282 | 5870 |
| MDCK permeability | nm/sec | 10000 | 10000 |
| Number of primary metabolites | | 2 | 4 |
| Rotatable bonds | | 1 | 1 |
| Human Oral Absorption | | low | low |

Four compounds (M3, M6, M11, and M12) proved active (FIG. 1J) in vitro. Three tested further were potent at 10-100× lower concentrations (FIG. 1K) and also promoted monolayer wound closure (FIG. 1L). The conclusions are that the 1-(2-morpholino-5-(trifluoromethyl)phenyl)urea moiety connected to an aromatic or saturated Ring D via CH plays a role in potency while Rings C and D can be further modified. Racemic mixtures were obtained the various forms can more active than others (chiral center at Ring C). Isosteric modification of Ring A is also an option.

The compounds can be synthesized by methods of organic synthesis.

Example 3

Compounds Promote Mucosal Healing in Models of Ischemic Ulceration and Indomethacin Mucosal Injury with Minimal Toxicity (A) The effects of dosing of compound D3 on murine intestinal ulcer healing was investigated. Brief serosal application of a filter paper disk soaked in dilute acetic acid was used to create well demarcated reproducible mucosal small bowel ulcerations without opening the bowel (47-49). In one study such murine ulcers were created, allowed 24 hours for recovery and ulcer formation, and then compound D3 was administered at 900 ug/kg Q6H for three days before sacrifice. At day 4, mice receiving D3 exhibited substantially smaller ulcers than those receiving only the DMSO vehicle (FIG. 2A), and the percentage of wound closure was markedly higher in D3-dosed mice (FIGS. 2B, 2C). Males and females responded similarly. Mice receiving either vehicle control or drug exhibited similar weight loss, presumably from the effects of anesthesia, the surgical procedure, and the ulcer (data not shown). Serum creatinine was not different, and while a slight elevation of ALT was observed in mice receiving the drug, it remained within the normal range (data not shown). Histological evaluation showed no differences between the kidneys or livers of mice receiving drug vs. vehicle (data not shown).

(B) Indomethacin ulcer healing. 15 mg/kg of indomethacin was administered subcutaneously, and treatment started with vehicle of drug 1 day after injury. At 4 days, ulcer area was calculated after sacrifice by morphometric analysis of photographs of the entire small bowel. D3 achieved a substantial and statistically significant reduction in ulcer area with D3 (FIG. 2D). Although the trend did not achieve statistical significance, D3-treated mice lost less weight in this model as in the acetic acid model, suggesting possible improved well-being related to D3 effects on healing and minimal gross toxicity.

BIBLIOGRAPHY

1. Loftus E V, Jr. Update on the Incidence and Prevalence of Inflammatory Bowel Disease in the United States. Gastroenterol Hepatol (N Y). 2016; 12(11):704-7.
2. Mortality GBD, Causes of Death C. Global, regional, and national age-sex specific all-cause and cause-specific mortality for 240 causes of death, 1990-2013: a systematic analysis for the Global Burden of Disease Study 2013. Lancet. 2015; 385(9963):117-71.
3. Cabodi S, Di Stefano P, Leal Mdel P, Tinnirello A, Bisaro B, Morello V, et al. Integrins and signal transduction. Adv Exp Med Biol. 2010; 674:43-54.
4. Yu C F, Sanders M A, Basson M D. Human caco-2 motility redistributes FAK and paxillin and activates p38 MAPK in a matrix-dependent manner. Am J Physiol Gastrointest Liver Physiol. 2000; 278(6):G952-66.
5. Basson M D, Sanders M A, Gomez R, Hatfield J, Vanderheide R, Thamilselvan V, et al. Focal adhesion kinase protein levels in gut epithelial motility. Am J Physiol Gastrointest Liver Physiol. 2006; 291(3):G491-9.
6. Walsh M F, Ampasala D R, Hatfield J, Vander Heide R, Suer S, Rishi A K, et al. Transforming growth factor-beta stimulates intestinal epithelial focal adhesion kinase synthesis via Smad- and p38-dependent mechanisms. Am J Pathol. 2008; 173(2):385-99.
7. Raschka S, More S K, Devadoss D, Zeng B, Kuhn L A, Basson M D. Identification of potential small-molecule protein-protein inhibitors of cancer metastasis by 3D epitope-based computational screening. J Physiol Pharmacol. 2018; 69(2).
8. Folkman J, Szabo S, Stovroff M, McNeil P, Li W, Shing Y. Duodenal ulcer. Discovery of a new mechanism and development of angiogenic therapy that accelerates healing. Ann Surg. 1991; 214(4):414-25; discussion 26-7.
9. Khan R I, Yazawa T, Anisuzzaman A S, Semba S, Ma Y, Uwada J, et al. Activation of focal adhesion kinase via M1 muscarinic acetylcholine receptor is required in restitution of intestinal barrier function after epithelial injury. Biochim Biophys Acta. 2014; 1842(4):635-45.
10. Fodor M, Price E, Wang P, Lu H, Argintaru A, Chen Z, et al. Dual Allosteric Inhibition of SHP2 Phosphatase. ACS Chem Biol. 2018; 13(3):647-56.
11. McNeil P L, Ito S. Gastrointestinal cell plasma membrane wounding and resealing in vivo. Gastroenterology. 1989; 96(5 Pt 1):1238-48.
12. Basson M D. Hierarchies of healing in gut mucosal injury. J Physiol Pharmacol. 2017; 68(6):789-95.
13. Singh P K, Negi A, Gupta P K, Chauhan M, Kumar R. Toxicophore exploration as a screening technology for drug design and discovery: techniques, scope and limitations. Arch Toxicol. 2016; 90(8):1785-802.
14. Lietha D, Cai X, Ceccarelli D F, Li Y, Schaller M D, Eck M J. Structural basis for the autoinhibition of focal adhesion kinase. Cell. 2007; 129(6):1177-87.
15. Brami-Cherrier K, Gervasi N, Arsenieva D, Walkiewicz K, Boutterin M C, Ortega A, et al. FAK dimerization controls its kinase-dependent functions at focal adhesions. EMBO J. 2014; 33(4):356-70.
16. Zhao X, Guan J L. Focal adhesion kinase and its signaling pathways in cell migration and angiogenesis. Adv Drug Deliv Rev. 2011; 63(8):610-5.
17. Thamilselvan V, Craig D H, Basson M D. FAK association with multiple signal proteins mediates pressure-induced colon cancer cell adhesion via a Src-dependent PI3K/Akt pathway. FASEB J. 2007; 21(8):1730-41.
18. Wang S, Basson M D. Akt directly regulates focal adhesion kinase through association and serine phosphorylation: implication for pressure-induced colon cancer metastasis. Am J Physiol Cell Physiol. 2011; 300(3): C657-70.
19. Craig D H, Owen C R, Conway W C, Walsh M F, Downey C, Basson M D. Colchicine inhibits pressure-induced tumor cell implantation within surgical wounds and enhances tumor-free survival in mice. J Clin Invest. 2008; 118(9):3170-80.
20. Zeng B, Devadoss D, Wang S, Vomhof-DeKrey E E, Kuhn L A, Basson M D. Inhibition of pressure-activated cancer cell adhesion by FAK-derived peptides. Oncotarget. 2017; 8(58):98051-67.
21. Chen Y N, LaMarche M J, Chan H M, Fekkes P, Garcia-Fortanet J, Acker M G, et al. Allosteric inhibition of SHP2 phosphatase inhibits cancers driven by receptor tyrosine kinases. Nature. 2016; 535(7610):148-52.
22. Owen K A, Abshire M Y, Tilghman R W, Casanova J E, Bouton A H. FAK regulates intestinal epithelial cell survival and proliferation during mucosal wound healing. PLoS One. 2011; 6(8):e23123.
23. Quiros M, Nusrat A. Contribution of Wound-Associated Cells and Mediators in Orchestrating Gastrointestinal Mucosal Wound Repair. Annu Rev Physiol. 2018.
24. Turowski G A, Rashid Z, Hong F, Madri J A, Basson M D. Glutamine modulates phenotype and stimulates proliferation in human colon cancer cell lines. Cancer Res. 1994; 54(22):5974-80.
25. Patani G A, LaVoie E J. Bioisosterism: A Rational Approach in Drug Design. Chemical Reviews. 1996; 96(8):3147-76.
26. Meanwell N A. Synopsis of Some Recent Tactical Application of Bioisosteres in Drug Design. Journal of Medicinal Chemistry. 2011; 54(8):2529-91.
27. Brown N. Bioisosteres in Medicinal Chemistry 2012.
28. Métayer B, Compain G, Jouvin K, Martin-Mingot A, Bachmann C, Marrot J, et al. Chemo- and Stereoselective Synthesis of Fluorinated Enamides from Ynamides in HF/Pyridine: Second-Generation Approach to Potent Ureas Bioisosteres. The Journal of Organic Chemistry. 2015; 80(7):3397-410.
29. Weller H N, Nirschl D S, Petrillo E W, Poss M A, Andres C J, Cavallaro C L, et al. Application of Lean Manufacturing Concepts to Drug Discovery: Rapid Analogue Library Synthesis. Journal of Combinatorial Chemistry. 2006; 8(5):664-9.
30. Lipinski C A. Lead- and drug-like compounds: the rule-of-five revolution. Drug Discovery Today: Technologies. 2004; 1(4):337-41.
31. Abraham C, Cho J H. MECHANISMS OF DISEASE Inflammatory Bowel Disease. N Engl J Med. 2009; 361 (21):2066-78.
32. Blasco V, Cuñat A C, Sanz-Cervera J F, Marco J A, Falomir E, Murga J, et al. Arylureas derived from colchicine: Enhancement of colchicine oncogene downregulation activity. European Journal of Medicinal Chemistry. 2018; 150:817-28.
33. Padiya K J, Gavade S, Kardile B, Tiwari M, Bajare S, Mane M, et al. Unprecedented "In Water" Imidazole Carbonylation: Paradigm Shift for Preparation of Urea and Carbamate. Organic Letters. 2012; 14(11):2814-7.
34. Concellón J M, Bernad P L, Rodríguez-Solla H, Concellón C. A Convenient Samarium-Promoted Synthesis of Aliphatic (E)-Nitroalkenes under Mild Conditions. The Journal of Organic Chemistry. 2007; 72(14):5421-3.
35. Southwick P L, Anderson J E. The Stereochemistry of Conjugate Additions. A Study of the Addition of Amines to (2-Nitropropenyl)-benzene. Journal of the American Chemical Society. 1957; 79(23):6222-9.
36. Moustakim M, Clark P G K, Trulli L, Fuentes de Arriba A L, Ehebauer M T, Chaikuad A, et al. Discovery of a PCAF Bromodomain Chemical Probe. 2017; 56(3):827-31.
37. Nayal O S, Bhatt V, Sharma S, Kumar N. Chemoselective Reductive Amination of Carbonyl Compounds for the Synthesis of Tertiary Amines Using SnCl2·2H2O/PMHS/MeOH. The Journal of Organic Chemistry. 2015; 80(11):5912-8.
38. Reddy N V, Kumar P S, Reddy P S, Kantam M L, Reddy K R. Synthesis of unsymmetrical phenylurea derivatives via oxidative cross coupling of aryl formamides with amines under metal-free conditions. New Journal of Chemistry. 2015; 39(2):805-9.
39. Chen J, Gong C, Mao H, Li Z, Fang Z, Chen Q, et al. E2F1/SP3/STAT6 axis is required for IL-4-induced epithelial-mesenchymal transition of colorectal cancer cells. Int J Oncol. 2018; 53(2):567-78.
40. Yeatman T J. A renaissance for SRC. Nat Rev Cancer. 2004; 4(6):470-80.
41. Nakamura K, Yano H, Schaefer E, Sabe H. Different modes and qualities of tyrosine phosphorylation of Fak and Pyk2 during epithelial-mesenchymal transdifferentiation and cell migration: analysis of specific phosphorylation events using site-directed antibodies. Oncogene. 2001; 20(21):2626-35.
42. Rydberg P, Gloriam D E, Olsen L. The SMARTCyp cytochrome P450 metabolism prediction server. Bioinformatics. 2010; 26(23):2988-9.
43. Rydberg P, Gloriam D E, Zaretzki J, Breneman C, Olsen L. SMARTCyp: A 2D Method for Prediction of Cytochrome P450-Mediated Drug Metabolism. ACS Medicinal Chemistry Letters. 2010; 1(3):96-100.
44. Rydberg P, Olsen L. Ligand-Based Site of Metabolism Prediction for Cytochrome P450 2D6. ACS Medicinal Chemistry Letters. 2012; 3(1):69-73.
45. Rydberg P, Olsen L. Predicting Drug Metabolism by Cytochrome P450 2C9: Comparison with the 2D6 and 3A4 Isoforms. 2012; 7(7):1202-9.
46. Bowes J, Brown A J, Hamon J, Jarolimek W, Sridhar A, Waldron G, et al. Reducing safety-related drug attrition: the use of in vitro pharmacological profiling. Nature Reviews Drug Discovery. 2012; 11:909.
47. Owen C R, Yuan L, Basson M D. Smad3 knockout mice exhibit impaired intestinal mucosal healing. Lab Invest. 2008; 88(10):1101-9.
48. Flanigan T L, Owen C R, Gayer C, Basson M D. Supraphysiologic extracellular pressure inhibits intestinal epithelial wound healing independently of luminal nutrient flow. Am J Surg. 2008; 196(5):683-9.
49. Kovalenko P L, Flanigan T L, Chaturvedi L, Basson M D. Influence of defunctionalization and mechanical forces on intestinal epithelial wound healing. Am J Physiol Gastrointest Liver Physiol. 2012; 303(10):G1134-43.
50. Fukumoto K, Naito Y, Takagi T, Yamada S, Horie R, Inoue K, et al. Role of tumor necrosis factor-alpha in the pathogenesis of indomethacin-induced small intestinal injury in mice. Int J Mol Med. 2011; 27(3):353-9.

All publications, patents and patent applications are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

What is claimed is:

1. A method to treat an epithelial disease comprising administering to a subject in need thereof an effective amount of a compound of Formula IX:

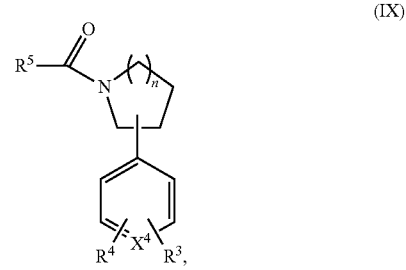

(IX)

wherein $X^4$ is —CH— or —N—; and $R^3$ and $R^4$ are independently chosen from —OH substituted or unsubstituted ($C_1$-$C_{20}$) hydrocarbyl;

$R^5$ is chosen from —H, —OH, and substituted or unsubstituted ($C_1$-$C_{20}$) hydrocarbyl; and n is 1 or 2.

2. The method of claim 1, wherein the ($C_1$-$C_{20}$)hydrocarbyl is chosen from ($C_1$-$C_{20}$)alkyl, ($C_1$-$C_{20}$)alkenyl, ($C_1$-$C_{20}$) alkynyl, ($C_1$-$C_{20}$)acyl, ($C_1$-$C_{20}$)cycloalkyl, ($C_1$-$C_{20}$)aryl, ($C_1$-$C_{20}$)haloalkyl, and combinations thereof.

3. A method to activate focal adhesion kinase phosphorylation in eukaryotic cells comprising contacting said cells with a compound of Formula IX,

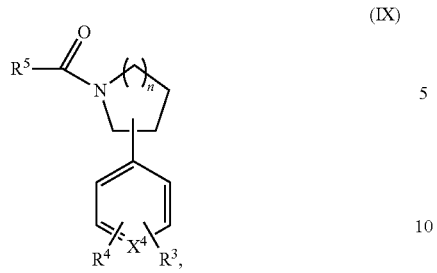
(IX)

wherein
$X^4$ is —N—; and
$R^3$ and $R^4$ are independently chosen from —H, —OH, —OCH$_3$, and substituted or unsubstituted (C$_1$-C$_{20}$) hydrocarbyl;
$R^5$ comprises the compound represented by Formula I:

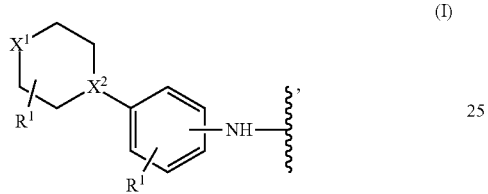
(I)

wherein
$X^1$ and $X^2$ are independently —C— or —N— and
at each occurrence $R^1$ is independently chosen from —H, —OH, and substituted or unsubstituted (C$_1$-C$_{20}$) hydrocarbyl.

4. The method of claim 3, wherein the (C$_1$-C$_{20}$)hydrocarbyl is chosen from (C$_1$-C$_{20}$)alkyl, (C$_1$-C$_{20}$)alkenyl, (C$_1$-C$_{20}$) alkynyl, (C$_1$-C$_{20}$)acyl, (C$_1$-C$_{20}$)cycloalkyl, (C$_1$-C$_{20}$)aryl, (C$_1$-C$_{20}$)haloalkyl, and combinations thereof.

5. A method to treat an epithelial disease comprising administering to a subject in need thereof an effective amount of a compound of Formula X:

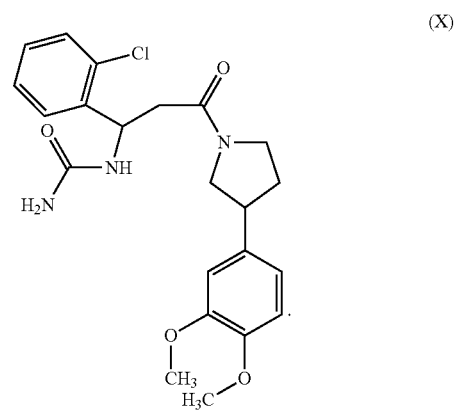 [SMILES: COc1ccc(C2CCN(C(=O)CC(NC(N)=O)c3ccccc3Cl)C2)cc1OC]
(X)

6. A method to activate focal adhesion kinase phosphorylation in eukaryotic cells comprising contacting said cells with a compound of Formula X:

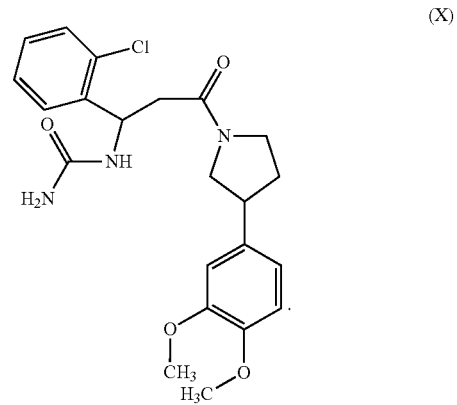 [SMILES: COc1ccc(C2CCN(C(=O)CC(NC(N)=O)c3ccccc3Cl)C2)cc1OC]
(X)

* * * * *